United States Patent
Bertelsen et al.

(10) Patent No.: US 10,485,715 B2
(45) Date of Patent: *Nov. 26, 2019

(54) PACKAGING FOR FORM-STABLE COILED COLLAGEN CARRIER

(71) Applicant: Takeda Nycomed AS, Asker (NO)

(72) Inventors: Poul Bertelsen, Roskilde (DK); Wolfgang Schonhofer, St. Polten (AT); Pernille Dybendal Pedersen, Frederiksberg (DK); Henrik Braender, Kalundborg (DK); Ingrid Blanka, Hellmonsodt (AT); Henrik Neuschafer Larsen, Soborg (DK); Siegfried Kirchmayr, Luftenberg (AT); Meinolf Vogt, St. Gotthard (AT)

(73) Assignee: TAKEDA AS, Asker (NO)

(*) Notice: Subject to any disclaimer, the term of this patent is extended or adjusted under 35 U.S.C. 154(b) by 0 days.

This patent is subject to a terminal disclaimer.

(21) Appl. No.: 14/401,681

(22) PCT Filed: May 22, 2013

(86) PCT No.: PCT/EP2013/060537
§ 371 (c)(1),
(2) Date: Nov. 17, 2014

(87) PCT Pub. No.: WO2013/174879
PCT Pub. Date: Nov. 28, 2013

(65) Prior Publication Data
US 2015/0136628 A1    May 21, 2015

(30) Foreign Application Priority Data

May 24, 2012  (WO) ................ PCT/DK2012/050178
Nov. 23, 2012  (EP) ..................................... 12194097

(51) Int. Cl.
*A61F 15/00*    (2006.01)
*A61B 50/00*    (2016.01)

(52) U.S. Cl.
CPC ............ *A61F 15/001* (2013.01); *A61B 50/00* (2016.02); *A61B 2050/005* (2016.02); *A61B 2050/0065* (2016.02); *B65D 2575/3218* (2013.01)

(58) Field of Classification Search
CPC .......... A61F 15/001; A61F 2/06; A61L 27/18; A61L 15/325; A61B 50/00;
(Continued)

(56) References Cited

U.S. PATENT DOCUMENTS 3,759,375 A    9/1973 Nappi
4,453,939 A    6/1984 Zimmerman et al.
(Continued)

FOREIGN PATENT DOCUMENTS

DE    195 46 435 A1    6/1997
DE    19546435 A1    6/1997
(Continued)

OTHER PUBLICATIONS

Bisertes, Jacques. "TachoSil: the value of its use in urologic surgerys" Journal De Chirurgie, Paris 2007 vol. 144(1), pp. 82-83.
(Continued)

*Primary Examiner* — Jacob K Ackun
*Assistant Examiner* — Jenine Pagan
(74) *Attorney, Agent, or Firm* — Nath, Goldberg & Meyer; Joshua B. Goldberg

(57) ABSTRACT

The present invention relates to a packaging for storing a form-stable coiled collagen carrier. The form-stable coiled collagen carrier comprises a collagen layer and a coating layer comprising thrombin and fibrinogen and having the shape of an elongated element with a number of windings of
(Continued)

the collagen carrier about the longitudinal axis of the elongated element with at least one outer winding(s) being orientated so that the coating layer constitutes the outer surface of each of said outer winding(s). The packaging preferably comprises a container part having a compartment in which at least a part of the coiled collagen carrier is contained.

27 Claims, 6 Drawing Sheets

(58) Field of Classification Search
CPC ...... A61B 2050/005; A61B 2050/0065; B65D 2575/3218
USPC ........ 206/438, 439, 440; 424/1.65; 427/2.31
See application file for complete search history.

(56) References Cited

U.S. PATENT DOCUMENTS

| | | | |
|---|---|---|---|
| 5,147,387 A | 9/1992 | Jansen et al. | |
| 5,290,310 A | 3/1994 | Makower et al. | |
| 5,810,711 A | 9/1998 | Scheyer | |
| 5,942,278 A | 8/1999 | Hagedorn et al. | |
| 5,990,379 A * | 11/1999 | Gregory | A61F 2/0063 128/898 |
| 6,177,126 B1 | 1/2001 | Hagedorn et al. | |
| 7,052,713 B2 | 5/2006 | Stimmeder | |
| 8,592,639 B2 * | 11/2013 | Utterberg | A61F 13/0203 206/441 |
| 9,446,103 B2 * | 9/2016 | Hakimimehr | A61K 9/7007 |
| 9,814,686 B2 * | 11/2017 | Schoenhofer | A61F 13/0276 |
| 2003/0176828 A1 | 9/2003 | Buckman et al. | |
| 2005/0155608 A1 | 7/2005 | Pavcnik et al. | |
| 2005/0178396 A1 | 8/2005 | Hunter et al. | |
| 2005/0183731 A1 | 8/2005 | Hunter et al. | |
| 2005/0186244 A1 | 8/2005 | Hunter et al. | |
| 2005/0187140 A1 | 8/2005 | Hunter et al. | |
| 2005/0196421 A1 | 9/2005 | Hunter et al. | |
| 2005/0208095 A1 | 9/2005 | Hunter et al. | |
| 2005/0214277 A1 | 9/2005 | Schaufler | |
| 2005/0234397 A1 | 10/2005 | Poff et al. | |
| 2008/0131473 A1 | 6/2008 | Brown et al. | |
| 2008/0215087 A1 * | 9/2008 | Pavcnik | A61B 17/0057 606/213 |
| 2009/0137042 A1 * | 5/2009 | Govil | A61F 2/0095 435/395 |
| 2009/0184026 A1 | 7/2009 | Massengale et al. | |
| 2009/0275129 A1 | 11/2009 | Cooper et al. | |
| 2010/0055149 A1 | 3/2010 | Li et al. | |
| 2010/0106068 A1 | 4/2010 | Karpiel et al. | |
| 2010/0155282 A1 * | 6/2010 | Govil | A61F 2/0095 206/438 |
| 2010/0254900 A1 * | 10/2010 | Campbell | A61L 27/18 424/1.65 |
| 2011/0040279 A1 | 2/2011 | Walsh | |
| 2011/0071424 A1 * | 3/2011 | Nock | A61B 19/54 600/562 |
| 2011/0140316 A1 * | 6/2011 | Bagga | A61F 2/28 264/571 |
| 2011/0144763 A1 * | 6/2011 | Bagga | A61L 27/427 623/23.61 |
| 2012/0052040 A1 | 3/2012 | Hunter et al. | |
| 2012/0125798 A1 * | 5/2012 | Baecker | B65D 81/266 206/524.1 |
| 2012/0207808 A1 | 8/2012 | Evans et al. | |
| 2013/0029030 A1 * | 1/2013 | Larsen | A61L 15/325 427/2.31 |
| 2014/0072612 A1 | 3/2014 | Schoenhofer et al. | |

FOREIGN PATENT DOCUMENTS

| | | |
|---|---|---|
| DE | 202006009712 U1 | 10/2007 |
| EA | 006686 B1 | 2/2006 |
| EP | 1053757 A1 | 11/2000 |
| EP | 2052746 A2 | 4/2009 |
| EP | 2163230 A1 | 3/2010 |
| GB | 422990 | 1/1935 |
| GB | 423017 | 1/1935 |
| GB | 487258 | 6/1938 |
| JP | 2004-73221 A | 3/2004 |
| JP | 2004-188037 A | 7/2004 |
| JP | 2004-520124 A | 7/2004 |
| JP | 2005-506110 A | 3/2005 |
| JP | 2007-159866 A | 6/2007 |
| JP | 2010-012127 A | 1/2010 |
| JP | 2014-519897 A | 8/2014 |
| RU | 2018540 C1 | 8/1994 |
| RU | 2118176 C1 | 8/1998 |
| RU | 2188206 C2 | 8/2002 |
| RU | 2235539 C1 | 9/2004 |
| WO | 94/13210 A1 | 6/1994 |
| WO | 9721383 A1 | 6/1997 |
| WO | 02/058750 A2 | 8/2002 |
| WO | 02058749 A2 | 8/2002 |
| WO | 02/070594 A2 | 9/2002 |
| WO | 03009764 A1 | 2/2003 |
| WO | 2006/044879 A2 | 4/2006 |
| WO | 2006/044882 A2 | 4/2006 |
| WO | 2006/119256 A2 | 11/2006 |
| WO | 2007/117855 A1 | 10/2007 |
| WO | 2009/109963 A1 | 9/2009 |
| WO | 2009/126870 A2 | 10/2009 |
| WO | 2009/134447 A1 | 11/2009 |
| WO | 2012159635 A1 | 11/2012 |

OTHER PUBLICATIONS

Lattouf et al. "Practical hints for hemostasis in laparoscopic surgery", Minimally Invasive Therapy, 2007, 16(1), pp. 45-51.

Liatsikos et al. "Cautery Free Nerve Sparing Extraperitoneal Endoscopic Radical Prostatecomy: The Use of TachoSil for Hemostasis". Journal of Endourology. 2006, 20(1), A294.

Murphy et al. "TachoSil is an Effective Haemostatic Aid During Laparoscopic Partial Nephrectomy in a Porcine Model". European Urology Supplements. 2006, 5(2), p. 329.

Nohuz, Erdogan, et al., "Efficiency of TachoSil to Prevent Postsurgical Adhesion Development on Laparoscopic Rat Model",Gynecol Surg, vol. 6, 2009, pp. 323-329.

Rane et al. "Evaluation of a Hemostatic Sponge (TachoSil) for Sealing of the Renal Collecting System in a Porcine Laparoscopic Partial Nephrectomy Survival Model". Journal of Endourology, 24(4), 2010.

Ahmed et al. BJUI Letters. Journal Compilation, 2009, 104, 269-272.

Brochuere, Wissenwertes ueber Tachosil für Operateure, Nycomed 2009.

Carbon et al. "Minimalinvasive Kinderchirurgie: Entwicklung and Fortschritt durch innovative Technologie". Kiln Padiatr. 2001. 213, pp. 99-103.

Carbon et al. "Fast-track Surgery of Recurrent Pneumothorax in Patients with Cystic Fibrosis—Superiority of Minimally Invasive Tissue Management (ATSS)". Medimond, 2007, pp. 15-28.

Carbon et al. "AMISA: innovative tissue management in MIS". Minimally Invasive Therapy & Allied Technologies. 1999, 8(5) 347-353.

Carbon et al. "Innovatives Gewebemanagement in der minimal invasiven Chirurgie". Medizin & Wissen, 2000. English Translation attached.

Erdogru et al. "Laparoscopic transvesical repair of recurrent vesicovaginal fistula using with fleece-bound sealing system". Archives of Gynecology and Obstetrics. 2008, 277, pp. 461-464.

Gordon, L.E., "The New Science of Strong Materials or Why You Don't Fall Through the Floor", 1976, pp. 38-43.

TachoSil. A guided tour. Brochure, 2007.

Nakajima et al. "A Simple Application Technique of Fibrin-Coated Collagen Fleece (TachoComb) in Laparoscopic Surgery". Surgery Today. 2007, 37, pp. 176-179.

(56) References Cited

OTHER PUBLICATIONS

Rickenbacher et al. "Efficacy of TachoSil a fibrin-based haemostat in different fields of surgery—a systemic review". Expert Opinion on Biological Therapy. 2009, 9(7), pp. 897-907.
Sanseverino et al. "Laparoscopic Partial Nephrectomy with Parenchimal Haemostasis with TachoSil Application". Journal of Endourology. 2009, 23, p. A362.
Slupski et al. Suture-Free Laparoscopic Partial Nephrectomy—Improvement of Hemostasis with Human Fibrinogen and Thrombin-Coated Collagen Patch (TachoSil). European Urology Supplements. 2010, 9(6), p. 636.
Van Dijk et al. "Haemostasis in laparoscopic partial nephrectomy: Current status". Minimally Invasive Therapy & Allied Technologies. 2007, 16(1), pp. 31-44.
Simo, et al., "Hemostatic Agents in Hepatobiliary and Pancreas Surgery: A Review of the Literature and Critical Evaluation of a Novel Carrier-Bound Fibrin Sealant (TachoSil)", ISRN Surgery, vol. 2012, 12 pages.
"Highlights of Prescribing Information", TachoSil (Absorbable Fibrin Sealant Patch), Initial U.S. Approval, 2010, twelve pages.
2016 Photograph of Endodock® apparatus in retracted configuration.
2016 Photograph of Endodock® apparatus in extended configuration.
Endodock® Instruction Leaflet by Nycomed.
Fukui-Atsushi Aomori Rinsanpu Shi_Journal of Aomori Society Obstectricians year 2007 vol. 22 No. 1 pp. 22-25 A case of laroscopically detected severe adhesion and diastasis caused by the fibronogen sheet placed at adenomyometectomy.
www.tachosil.com copyrighted 2014.
Carbon, RT et al., "Tissue Sealing Concept in Minimally Invasive Surgery in Children", Pediatric Endosurgery & Innovative Techniques, vol. 5, Issue 1, pp. 5-12, (Jul. 8, 2004).
Carbon, RT et al. "AMISA: Innovative tissue management in MIS", Minimally Invasive Therapy & Allied Technologies, vol. 8, Issue 5, pp. 347-353, (Jul. 10, 2009).
Saif, R et al., "Use of Fibrin-Based Sealants and Gelatin-Matrix Hemostats in Laparoscopic Liver Surgery", Surgical Laparoscopy, Endoscopy & Percutaneous Techniques, vol. 21, Issue 3, pp. 131-141 (Jun. 2011).
Lee, MGM et al. "Application of Fibrin Sealant in Surgery", Surgical Innovation, vol. 12, No. 3, pp. 203-213 (2005).
Somil R et al. "Newer Haemostats in Cannine Practice", International Journal of Agricultural Sciences and Veterinary Medicine, vol. 1, No. 3, pp. 88-94 (Aug. 2013).
Wheat, JC et al. "Advances in Bioadhesives, Tissue Sealants, and Heostatic Agents", Urologic Clinics of North America, Elsevier (2009).
De Cogain, MR et al. "Advances in Tubeless Percutaneous Nephrolithotomy and Patient Selection: An Update", Current Urology Reports, Springer Link, vol. 14, Issue 2, pp. 130-137 (Apr. 2013).
Lewis, KM et al. "Control of bleeding in surgical procedures: critical appraisal of HEMOPATCH (Sealing Hemostat)", Medical Devices: Evidence and Research, Dove Press, issue 9, pp. 1-10, (2016).
Liu T et al. "Comparison of the Nuss and sternal turnover procedures for primary repair of pectus excavatum" Asian Journal of Surgery, vol. 37, pp. 30-34 (2014).
Singh I "Robot-assisted laparoscopic partial nephrectomy: Current review of the technique and literature", Journal of Minimal Access Surgery, vol. 5(4), pp. 87-92 (Oct.-Dec. 2009).
2016 Iran Search Results from counter-part Iran No. 13915014000301810.
Russian office action dated Feb. 2, 2017 for corresponding Russian Patent Application No. 2014907745 with English translation attached.

\* cited by examiner

PACKAGING FOR FORM-STABLE COILED COLLAGEN CARRIER

This application is filed under 35 U.S.C. 371 as the US national stage of PCT/EP2013/060537, filed May 22, 2013, which claims priority to PCT/DK2012/050178, filed May 24, 2012 and EP 12194097.7, filed Nov. 23, 2012.

TECHNICAL FIELD OF THE INVENTION

The present invention relates to a packaging for storing a form-stable coiled collagen carrier. The form-stable coiled collagen carrier comprises a collagen layer and a coating layer comprising thrombin and fibrinogen and having the shape of an elongated element with a number of windings of the collagen carrier about the longitudinal axis of the elongated element with at least one outer winding(s) being orientated so that the coating layer constitutes the outer surface of each of said outer winding(s). The packaging preferably comprises a container part having a compartment in which at least a part of the coiled collagen carrier is contained. The compartment has an opening provided in an upper surface of the container part. The container part preferably comprises at least one cavity situated at the rim of the opening, wherein said cavity opens into the compartment and into the upper surface.

BACKGROUND OF THE INVENTION

Medicated sponges are used during open surgery to stop local bleeding (hemostasis/haemostasis). They react upon contact with blood, other body fluids or saline to form a clot that glues the sponge to the tissue surface and hemostasis is reached in a few minutes. Medicated sponges are sponges, such as a collagen carrier as defined below, such as a cellulose sponge as disclosed in EP2052746.

Collagen has been used as a haemostatic agent for decades. A product that combines the haemostatic features of fibrin glue with the asset of collagen as a carrier has been developed and manufactured under the trademark Tacho-Sil®. TachoSil® is a ready-to-use collagen carrier with a coating of the active components of fibrin glue: human fibrinogen and human thrombin. The product is described in WO 02/058 749, WO 02/070 594 and WO 02/058 750.

TachoSil® contains fibrinogen and thrombin as a dried coating on the surface of a collagen sponge. In contact with body fluids, e.g. blood, lymph or physiological saline solution the components of the coating dissolve and partly diffuse into the wound surface. This is followed by the fibrinogen-thrombin reaction which initiates the last phase of physiological blood coagulation. Fibrinogen is converted into fibrin monomers which spontaneously polymerise to a fibrin clot, which holds the collagen sponge tightly to the wound surface.

TachoSil® has been sold since 2004 by Nycomed and is used in open surgery for hemostasis and sealing. Traditional open surgery usually requires a long incision of the skin.

Contrary to open surgery, a minimally invasive procedure is any procedure (surgical or otherwise) that is less invasive than open surgery used for the same purpose. Minimally invasive surgery (MIS) procedures are performed through one or more access orifices e.g. short incisions ('keyhole surgery') or through natural body openings. Hence, MIS procedures require specially designed surgical instruments which are placed through these access orifices. In abdominal surgery, the access of the instruments is usually done through so-called trocars, which are mostly rigid tubes with a typical inner diameter of 5 to 12 mm. The small size of the access orifices used in MIS restricts what can be inserted into the orifices. Therefore, all surgical tools and materials used in MIS procedures must be of a size and condition that allow for their insertion through the access orifices and they need, of course, as all medical tools to be sterile. Hence, tools and materials are most often specially designed for use in MIS.

WO 97/21383 (Nycomed Arzneimittel GmbH) discloses a surgical instrument comprising an applicating member, wherein the applicating member comprises a rodshaped portion so as to allow a sheet of surgical material such as, e.g. TachoComb® (coated equine collagen sponge/Nycomed) to be rolled up to form a carpetlike roll of surgical material on the rod-shaped portion of the applicating member. However, this manual instrument for hand-rolling surgical materials, such as collagen carriers, has several disadvantages as described below. WO 02/058749 discloses the non-sterile insertion of TachoComb® into an endoscopic equipment, wherein the sample is flattened manually to be able to wrap it manually around a guiding "pin". WO 02/058749 teaches that the collagen product "has to stay flexible enough in dry condition to be bent and rolled up" (p29, lines 19-20). Thus WO 02/058749 only relates to manual (i.e. hand-rolled), non-sterile rolling of TachoComb® and further teaches that the rolling process must be "dry". One significant problem with the above methods which use an applicating member or guiding pin for hand-coiling the collagen carrier arises in case application of multiple rolled/coiled collagen carriers is necessary in quick succession (e.g. either because one collagen carrier is insufficient to completely stop the bleeding, or due to an error in application of the first collagen carrier(s)). In this instance the same applicating member cannot be used to apply the second collagen carrier: instead, multiple applicating members must be prepared. This is because in order to apply collagen-based products such as the TachoComb® product correctly, the applicating member must be completely dry in order to avoid activating the adhesive properties of the collagen carrier. If the collagen carrier becomes prematurely wet by contacting a wet application member or guiding pin, the carrier will stick to the applicating member/guiding pin and/or become an unusable sticky lump of material. Another way of rolling up collagen-based surgical sheets is for the surgeon to use his/her hands in the same way as for rolling up a cigarette, however for this and all the manually-rolled cases above the rolled surgical product is not form-stable and is therefore more difficult to manipulate in a controlled manner after insertion into the body: the non-form-stable product may "spring open" in an uncontrolled way during the unrolling process and adhere incorrectly. This is a particular issue for MIS surgery, where it is harder to manipulate the product once it is in the body as one only has indirect access to the surgical sheet via endoscopic surgical instruments. One way of lessening the effect of the rolled collagen-based surgical product being non-form-stable is to tie the rolled product together with a suture, however this solution is only relevant where the coiled carrier in not unrolled in vivo but rather maintained in the patient in a coiled state (e.g. in a partial nephrectomy procedure).

As it is has been possible according to the invention to produce a coiled collagen carrier and in particular a form stable coiled collagen carrier there exist a need for storing such coiled collagen carrier. Some of the issues to be considered when providing means suitable as packagings are that the coiled collagen carrier should be easy removable from the packaging and that the coiled collagen carrier being a rather fragile element should at least to some extent be protected, for example to protect the coating from flaking off.

SUMMARY OF THE INVENTION

It is an object of the present invention to provide a packaging for a coiled collagen carrier.

The present invention relates in a first aspect to a packaging for storing a form-stable coiled collagen carrier; the form-stable coiled collagen carrier comprising a collagen layer and a coating layer comprising thrombin and fibrinogen and having the shape of an elongated element with a number of windings of the collagen carrier about the longitudinal axis of the elongated element with at least one outer winding(s) being orientated so that the coating layer constitutes the outer surface of each of said outer winding(s). The packaging comprises
  a container part having a compartment in which at least a part of the coiled collagen carrier is contained, the compartment having an opening provided in an upper surface of the container part, and
  at least one cavity situated at the rim of the opening, wherein said cavity opens into the compartment and into the upper surface.

In preferred embodiments, the invention relates to a packaging for storing a form-stable coiled collagen carrier, wherein said packaging contains a form-stable coiled collagen carrier, said form-stable coiled collagen carrier comprising a collagen layer and a coating layer comprising thrombin and fibrinogen and having the shape of an elongated element with a number of windings of the collagen carrier about the longitudinal axis of the elongated element with at least one outer winding(s) being orientated so that the coating layer constitutes the outer surface of each of said outer winding(s). The packaging comprising
  a container part having a compartment in which at least a part of the coiled collagen carrier is contained, the compartment having an opening provided in an upper surface of the container part, and
  at least one cavity situated at the rim of the opening, wherein said cavity opens into the compartment and into the upper surface.

Preferably, the opening is generally rectangular shaped, wherein the length and the width of the opening are larger than the respective length and the diameter of the coiled collagen carrier.

In preferred embodiments, a cavity is situated at one of the shorter sides of the opening. Alternatively or in combination thereto, a cavity is situated at one of the longer sides of the opening.

Preferably, the cavity comprises a wall section extending from a position at the upper surface outside the rim of the opening and towards the bottom of the compartment, such as at least half-way down the height of the compartment, wherein the wall section of the cavity extends sloped or curved.

In preferred embodiments of the present invention, the packaging may comprise a cover covering the opening of the packaging. Such a cover may preferably be attached to the container part in a manner allowing manual removal of the cover, such as by use of fingers. The cover may preferably be attached by heat welding or gluing to the upper surface of the container part.

Preferably, the cover may be attached to the container part along an outer rim of the container part encircling the opening and the cavity.

The cover may preferably have a pull-tab not being attached to the container part.

The cover may preferably be gas and/or liquid permeable. The cover may preferably be made from a medical grade high density polyethylene sealing cover foil.

In preferred embodiments, the container part may be sheet-shaped with the compartment as well as the cavity being formed as indentations in the sheet.

The container part can preferably be made from one or more plastic(s), such as a thermoplastic plastic, preferably a thermoplastic polyester, for example selected from PBT (polybutylene terephthalate), PETG (polyethylene terephtalate glycol-modified) and PET (polyethylene terephthalate), preferably PET Alternatively or in combination thereto, the material of the container part can be made from pvc and/or an x-ray detectable plastic, polyurethane, or nylon coated with Polyurethane) and/or flexible foils, such as aluminium foil. Surgical grade plastics are one preferred group of suitable waterproof material, such as e.g. surgical grade polyvinyl chloride (pvc), polyethylene terphthalate, polyurethane and also surgical grade silicone rubber materials The container part may preferably be thermoformed by e.g. injection moulding, blow moulding, vacuum moulding or rotational moulding.

In many preferred embodiments, the packaging, the upper surface of the container part may be horizontal, and the compartment may be cuboid shaped. The compartment thereby has a horizontal bottom, two vertical side walls and a vertical end wall extending from the upper surface and to the bottom of the compartment, in cases where the cavity is arranged at the end wall.

Preferably, the intersections of the bottom with the side walls and the end wall respectively may be rounded.

The cavity may preferably extend from the horizontal level of the upper surface and towards the bottom of the compartment, such as at least half-way down the height of the compartment.

Preferred embodiments of a packaging according to present invention may further comprise a second container inside which the container part with coiled collagen carrier and the cover is arranged. The second container may preferably be made from a fluid tight material and is fluid-tight when closed.

A packaging according to the present invention may further comprise a desiccant arranged inside the second container and outside the container part with coiled collagen carrier and the cover.

The second container may preferably be in the form of a pouch inside which the container part with coiled collagen carrier and the cover and the desiccant are arranged. The pouch is preferably tear-openable or pull-openable.

Preferably, the second container is made from a foil comprising or consisting of metal such as aluminium, plastic coated metal, or the like.

A packaging according to the present invention may further comprise one or more supporting elements defining a set of support points or surfaces distributed in a common horizontal plane below or at the level as the outer surface of the bottom of the compartment. Such support points or surfaces may preferably be distributed outside the bottom.

The supporting elements may preferably be downwardly protruding elements formed as indentations in the container part. The indentation may therefore provide cavities which according to preferred embodiments are left empty in packaging according to the present invention, that is no elements are arranged in the cavities.

In preferred embodiments, the support points or surfaces may be contained in a circumscribed rectangle of which the support points or a corner of each surface define the corners of the circumscribed rectangle and wherein the geometrical centre of the circumscribed rectangle and the geometrical centre of the outer surface of the bottom of the compartment coincide.

DEFINITIONS

Prior to discussing the present invention in further details, the following terms and conventions will first be defined:

The term "collagen carrier" is in the present context any suitable carrier comprising collagen that can have a coating layer that comprises/consists of a collagen layer and/or a coating layer. The collagen carrier can in one embodiment be rolled or coiled (the words "rolled" and "coiled" are used interchangeably herein). The collagen carrier can in another embodiment be in an unrolled or uncoiled state after coiling, i.e. as an unrolled or uncoiled collagen carrier (the terms "unroll" or "uncoil" are used interchangeably herein). The coiled collagen carrier of the present invention can in one embodiment be a compressed, coiled collagen carrier, or in another embodiment an unrolled version of a compressed, coiled collagen carrier. Preferably, the collagen carrier is a collagen sponge comprising or consisting essentially of collagen type I fibres and a coating.

Although the carrier material is preferably a collagen sponge which comprises collagen type I material from mammalian, transgenic or recombinant sources, it can also comprise another type of collagen, for example one or more of collagen type I, II, III, IV, VII and/or X. Preferably the collagen carrier, such as a collagen sponge, is coated with the human coagulation factors fibrinogen and thrombin and optionally also riboflavin (a yellow colouring agent used to aid in identifying the active side of the collagen carrier). Thus in one embodiment of the present invention, the collagen carrier is a collagen sponge consisting essentially of collagen type I fibres and a coating of fibrinogen, thrombin and riboflavin. Fibrinogen and thrombin can for example be human fibrinogen and thrombin, and can be purified from a natural source, or can alternatively be e.g. transgenic or recombinant human fibrinogen and thrombin, or can be manufactured by other methods such as e.g. chemical synthesis. Fibrinogen and thrombin are preferably solid or mostly solid and in one embodiment can be human of origin. In another embodiment, at least one and more preferably both of the components fibrinogen and thrombin have the human amino acid sequence and can be produced by recombinant technology, inclusion bodies or chemical synthesis. The thrombin and fibrinogen are in one embodiment dry, such as containing less than 5% water, such as less than 4% water, such as less than 3% water, such as less than 2% water, such as less than 1% water, such as less than 0.8% water, such as less than 0.6% water, such as less than 0.4% water, such as less than 0.2% water, such as less than 0.1% water.

In one embodiment of the present invention, the collagen carrier comprises or consists of (i) a collagen layer and (ii) a coating layer comprising fibrinogen and optionally a colouring agent such as e.g. riboflavin. The collagen carrier may in an embodiment further comprise other peptides, such as other peptides capable of causing haemostasis.

In one embodiment of the present invention, the expressions collagen sponge, collagen fleece, collagen patch or simply fleece or patch are terms that are used synonymously to mean a collagen carrier. A carrier may alternatively to collagen comprise a biodegradable co-polymer or a polymer such as a polyhyaluronic acid, polyhydroxy acid, e. g. lactic acid, glucolic acid, hydroxybutanoic acid, a cellulose, or gelatine. Another alternative carrier may be polyglactin 910, i.e. a synthetic, adsorbable copolymer of 90% glycolide ($C_2H_2O_2$) and 10% lactide ($C_6H_8O_4$); such as e.g. with molecular formula $(C_2H_2O_2)_m$ and $(C_3H_4O_2)_n$. A further alternative carrier may be equine collagen, such as e.g. native equine collagen extracted from sinews or tendons.

Thus, the collagen part of the collagen carrier can in one embodiment of the present invention be substituted with a non-collagen matrix that is coated in the same way as for the collagen carrier as described herein, i.e. in one embodiment of the present invention is provided a carrier comprising or consisting of a non-collagen matrix coated with a coating comprising or consisting of fibrinogen and thrombin. One example of a suitable non-collagen matrix is a cellulose fabric. In one embodiment of the present invention, the non-collagen matrix is an oxidized regenerated cellulose fabric sheet attached to a non-woven polyglactin 910 felt.

However, it is preferably a collagen carrier preferably having a shape suitable for a medicated sponge. In an embodiment of the invention, the collagen carrier which is to undergo the coiling process of the present invention is identical to Tachosil® or TachoComb® available from Nycomed, such as described in WO 02/058 749, WO 02/070 594 and WO 02/058 750.

A preferred collagen layer is preferably used to mean a collagen sponge produced by the method according to the invention as disclosed in WO 02/070594. The collagen layer used in the present invention preferably fulfills at least one, such as at least two or at least three, of the following criteria:
  pH-value between 5.0 and 6.0,
  lactic acid content at the most 5%,
  ammonium content at the most 0.5%,
  soluble protein content, calculated as albumin content, at the most 0.5%,
  sulphate ashes content at the most 1.0%,
  heavy metal content at the most 20 ppm,
  microbiological purity, at the most 103 CFU/g,
  collagen content of 75% to 100%,
  density of 1-10 mg/cm$^3$, such as 2-7 mg/cm$^3$,
  elasticity module of 5-100 N/cm$^2$, such as 10-50 N/cm$^2$,
    and wherein when isolating parts of the sponge, the sponge will have the following properties:
  elasticity module in the range of 5 to 100 N/cm$^2$,
  density in the range of 1 to 10 mg/cm$^3$,
  chamber diameter of more than 0.75 mm and less than 4 mm, or a chamber diameter average of at most 3 mm.

Please note that the density of a collagen carrier is the density of the collagen carrier excluding the coating layer.
  Preferably the collagen layer fulfills at least the following:
  pH-value between 5.0 and 6.0,
  lactic acid content at the most 5%,
  ammonium content at the most 0.5%,
  soluble protein content, calculated as albumin content, at the most 0.5%,
  sulphate ashes content at the most 1.0%,
  heavy metal content at the most 20 ppm,
  microbiological purity, at the most 103 CFU/g,
  collagen content of 75% to 100%,
  density of 1-10 mg/cm$^3$, such as 2-7 mg/cm$^3$.

Further, the collagen layer is air and liquid tight in the sense that, once the collagen sponge is applied to a wound, it will not allow air or liquid to pass through the collagen layer. Liquids are absorbed in the layer. This effect is primarily achieved due to the fact the collagen layer has a three-dimensional structure with stacked chambers separated and substantially totally enclosed by walls of collagen material, in contradiction to known collagen sponges which have a fibre structure.

In the present context, the term "chamber diameter" should be understood as the largest straight-line wall-to-wall distance in a chamber, i. e. as the largest diagonal straight-line distance of a chamber. The chambers may be of a polygonal shape, such as of an octagonal shape. Thus, when the carrier is cut, the chambers are divided and cut to caverns.

It has been found that a chamber diameter of more than 0.75 mm and less than 4 mm, or a chamber diameter average of at most 3 mm, renders the collagen sponge particularly useful for being coated with a fibrin glue preparation. When the carrier is cut, the chambers are divided and cut to caverns. The preferably solid fibrinogen and the preferably solid thrombin is fixed to the collagen layer and most of it is present in the caverns thus providing a substantially even distribution of the preferably solid thrombin and preferably solid fibrinogen. Due to this and the fixation, it is possible to introduce substantial amounts of fibrinogen and thrombin on the carrier in contrast to the situation where liquid compositions of thrombin and fibrinogen are e. g. dropped or sprayed onto the material.

Each coated collagen carrier as well as the uncoated collagen layer is inspected visually for the "pore size distribution"—no pores wider than 4 mm and deeper than 2 mm are allowed. These sizes are measured with a ruler if necessary.

By fixation of the coating layer to the collagen layer is preferably meant that the coating layer adheres through mechanical interactions i.e. by inclusion onto the collagen carrier pore surface and within the coating layer.

In a preferred embodiment of the present invention, the amount of fibrinogen and thrombin/cm$^2$ in the coating layer can be:

Thrombin 1.3-2.7 IU/cm$^2$ and/or
Fibrinogen 3.6-7.4 mg/cm$^2$

In an embodiment, the above mentioned amounts of fibrinogen and thrombin/cm$^2$ are identical to Tachosil® or TachoComb® available from Nycomed, such as described in WO 02/058 749, WO 02/070 594 and WO 02/058 750.

By substantially even distribution of the solid thrombin and solid fibrinogen is meant that the coating layer is substantially evenly distributed across the collagen layer meaning that local changes in thickness of the coating layer is observed visually by SEM cross sections i.e. the coating layer may be located on the surface and sometimes at a lower level in an open cell. There should not be any through-going cracks (fissures) on the coating layer.

In an embodiment a collagen carrier according to the present invention may have a size of 92-98 mm*46-50 mm*4-7 mm and this carrier is called a large size collagen carrier and has the shape of a box of rectangular cross-section with all sides flat. Hence, the area of the largest rectangular cross-section is about 42.3-49.0 cm$^2$. In another embodiment a midi size collagen carrier according to the present invention is 46-49 mm*46-50 mm*4-7 mm, and has the shape of a square box of quadrant cross-section. Hence, the area of the quadrant cross-section is about 21.2-24.5 cm$^2$. A midi size collagen carrier according to the invention is preferred. In yet another embodiment a mini size collagen carrier according to the invention is 28-33 mm*23-27 mm*4-7 mm, and has the shape of a box of rectangular cross-section with all sides flat. Hence, the area of the largest rectangular cross-section is about 6.4-8.9 cm$^2$.

In an embodiment of the invention, a collagen carrier has at least one of the following physical properties, such as at least two of the following physical properties, such as at least three of the following physical properties, such as at least four of the following physical properties: elasticity module in the range of 5-100 N/cm$^2$, density of 1-10 mg/cm$^3$, chamber diameter of more than 0.75 mm and less than 4 mm and/or having a chamber diameter average below 3 mm and evenly distributed and fixed upon said collagen carrier solid fibrinogen and solid thrombin. Please note that the density of a collagen carrier is the density of the collagen carrier excluding the coating layer.

The term "mechanically" is meant to refer to any non-manual way of producing, obtaining or providing a medicated sponge, such as a rolled and/or compressed collagen carrier of the present invention by way of an at least semiautomatic process, such as a fully automatic process.

"Mechanically stable" is meant to refer to "form-stable".

Form-stable as used in form-stable coiled collagen carrier is preferably used to mean a coiled collagen carrier which maintains its geometrical shape without being fixated by constraining or constriction elements not forming part of the collagen carrier. For example, a form-stable coiled collagen carrier may maintain its geometrical shape because the coating layer and/or the collagen layer has no tension acting to distort—such as uncoil—the coiled collagen carrier. A further characteristic of form-stable is that the coiled collagen carrier may be elastic deformed and revert to the shape it had before being elastic deformed by the releasing the tension provided by the elastic deformation. A furthermore characteristic of a form-stable coiled collagen carrier is that it is preferably hardened in the coiled shape.

Solid as used e.g. solid fibrinogen and solid thrombin is used in a manner being ordinary to the skilled person to mean a material in solid state. Mostly solid is preferably used to that a minor fraction of the material in question may be in a state being different from solid state (such as less than 5%, such as less than 3%, preferably less than 1%, such as less than 0.5%). Alternatively, mostly solid is preferably used to mean that the material in question may contain liquid, such as less than 5% liquid, or less than 1% liquid.

The term "manual" is meant to refer to any manual way of producing, obtaining or providing a carrier, such as medicated sponge or such as a rolled and/or compressed collagen carrier of the present invention. Thus, by "manual" is meant any way in which at least one step of the production method (for example, the rolling step and/or the compression step) is carried out using at least one human hand(s), for example rolling the collagen fleece round a "pin" by hand or compressing the collagen fleece using hand power, for example compressing the fleece directly by application of one or more human hands. In a preferred embodiment of the present invention, at least the rolling step and/or the compression step are not carried out manually, i.e. are not carried out by using human hand(s). Thus in a preferred embodiment of the present invention, the collagen fleece is not rolled around an object (such as a pin) by hand and/or the collagen fleece is not compressed by the application of at least one human hand.

By the term "rolling" is meant any well known process for rolling an object i.e. by hand, mechanically or by a combination thereof.

Coiling as used e.g. in coiling said collagen carrier is preferably used to mean the process of winding the collagen carrier into an element preferably having spiral shaped cross sections. The coiled collagen carrier may have an S-shaped core.

For example, the rolled collagen carrier can have a diameter of at the most 12 mm, such as at the most 11 mm, such as at the most 10 mm, for example at the most 8 mm, such as at the most 6 mm, for example at the most 4 mm and optionally a sterility assurance level (SAL) of $10^{-6}$.

By the term "rolled compressed collagen carrier" is meant a rolled compressed collagen carrier characterized by the following physical properties: a coating comprising solid fibrinogen and solid thrombin that is evenly distributed and fixed upon said collagen carrier, and having at least one of the following physical properties:

I. a diameter of at the most 10 mm
II. a sterility assurance level (SAL) of $10^{-6}$.

Thus, an advantage of the invention is that said rolled compressed collagen carrier is ready to use in minimally invasive surgery, such as ready to be inserted into endoscopic devices.

By the term "mechanically rolled compressed collagen carrier" is meant a collagen carrier that has been mechanically compressed and thereafter mechanically rolled and which is characterized by the following physical properties: a coating comprising solid fibrinogen and solid thrombin that is evenly distributed and fixed upon said mechanically rolled compressed collagen carrier, and having at least one of the following physical properties:

I. a diameter of at the most 10 mm
II. a sterility assurance level (SAL) of $10^{-6}$.

By the term "humidifying or humidification" is meant the process of humidifying/moisturizing at least part of a collagen carrier with at least one liquid solvent to preferably at least one side of said carrier which has at least one side coated with a coating comprising biologically active substances. If more than one side of the carrier is coated with a coating comprising biologically active substances, then the term may comprise humidifying such as at least two sides, such as at least three sides, such as at least four sides, such as at least five sides, such as all sides of said collagen carrier. The humidified side is preferably the side comprising a coating, but it may also be a side that does not comprise a coating.

Humidifying as used in e.g. humidifying at least a part of said collagen carrier is preferably also used to mean the step of applying a liquid substance to a collagen carrier.

Thus, the term "humidified collagen carrier" is meant to mean a collagen carrier that has been exposed to at least one liquid solvent to preferably at least one side of said carrier, such as at least two sides, such as at least three sides, such as at least four sides, such as at least five sides, such as all sides, to achieve a humidified collagen carrier.

In an embodiment of the present invention said humidified collagen carrier has a coating comprising solid fibrinogen and solid thrombin that is evenly distributed and fixed upon said collagen carrier, and having at least one of the following physical properties:

I. a diameter of at the most 10 mm
II. a sterility assurance level (SAL) of $10^{-6}$.

By the term "elasticity module" is meant the tendency of an object to be deformed elastically i.e., non-permanently when a force is applied to it. In the present context the elasticity module is used to describe the elasticity of a collagen carrier of the present invention. The elasticity module is in the present invention measured in $N/cm^2$. The elasticity module is preferably 5-100 $N/cm^2$, such as 15-90 $N/cm^2$, such as 25-80 $N/cm^2$, such as 35-70 $N/cm^2$, such as 45-60 $N/cm^2$, such as 50-55 $N/cm^2$. The elasticity module is a well known parameter in the art to measure elasticity, as disclosed in e.g. the book by J. E. Gordon, The New Science of Strong Materials or Why You Don't Fall Through the Floor page 38-43 and EP 1 053 757 B1. Elasticity module thus represents the elastic flexibility of a material, the flexibility of any given object.

By "elasticity module" is meant Youngs modul, E, the physical constant, characterized by the stiffness of an elastic material. E is force (N) divided with area ($mm^2$), written as $N/mm^2$ or MPa.

By the term "density" or the mass density of a material is meant the material's mass per unit volume. The symbol most often used for density is p but in the present context, density is defined as weight per unit volume $mg/cm^3$, which is also called specific weight. The method and the equipment used for determining the density are disclosed in further detail in the example section below. The density of a collagen carrier according to the present invention is the density of the collagen carrier excluding the coating layer.

The density of a humidified and/or compressed and/or rolled collagen carrier of the present invention is preferably in the range of 1-15 $mg/cm^3$, such as in the range of 2-15 $mg/cm^3$, such as in the range of 3-15 $mg/cm^3$, such as in the range of 4-15 $mg/cm^3$, such as in the range of 5-15 $mg/cm^3$, such as in the range of 6-15 $mg/cm^3$, such as in the range of 7-15 $mg/cm^3$, such as in the range of 8-15 $mg/cm^3$, such as in the range of 9-15 $mg/cm^3$, such as in the range of 10-15 $mg/cm^3$, such as in the range of 11-15 $mg/cm^3$, such as in the range of 12-15 $mg/cm^3$, such as in the range of 13-15 $mg/cm^3$, such as in the range of 14-15 $mg/cm^3$, such as in the range of 3-14 $mg/cm^3$, such as in the range of 3-12 $mg/cm^3$, such as in the range of 3-10 $mg/cm^3$, such as in the range of 3-9 $mg/cm^3$, such as in the range of 3-8 $mg/cm^3$, such as in the range of 3-7 $mg/cm^3$, such as in the range of 3-6 $mg/cm^3$, such as in the range of 3-5 $mg/cm^3$, such as in the range of 3.0-4.5 $mg/cm^3$, such as in the range of 3.0-4.4 $mg/cm^3$, such as in the range of 3.0-4.3 $mg/cm^3$, such as in the range of 3.0-4.2 $mg/cm^3$, such as in the range of 3.0-4.1 $mg/cm^3$, such as in the range of 3.0-4.0 $mg/cm^3$, such as in the range of 3.0-3.9 $mg/cm^3$, such as in the range of 3.0-3.8 $mg/cm^3$, such as in the range of 3.0-3.7 $mg/cm^3$, such as in the range of 3.0-3.6 $mg/cm^3$, such as in the range of 3.0-3.5 $mg/cm^3$, such as in the range of 3.0-3.4 $mg/cm^3$, such as in the range of 3.0-3.3 $mg/cm^3$, such as in the range of 3.0-3.2 $mg/cm^3$, such as in the range of 3.0-3.1 $mg/cm^3$, such as in the range of 3.1-4.5 $mg/cm^3$, such as in the range of 3.2-4.5 $mg/cm^3$, such as in the range of 3.3-4.5 $mg/cm^3$, such as in the range of 3.4-4.5 $mg/cm^3$, such as in the range of 3.5-4.5 $mg/cm^3$, such as in the range of 3.6-4.5 $mg/cm^3$, such as in the range of 3.7-4.5 $mg/cm^3$, such as in the range of 3.8-4.5 $mg/cm^3$, such as in the range of 3.9-4.5 $mg/cm^3$, such as in the range of 4.0-4.5 $mg/cm^3$, such as in the range of 4.1-4.5 $mg/cm^3$, such as in the range of 4.2-4.5 $mg/cm^3$, such as in the range of 4.3-4.5 $mg/cm^3$, such as in the range of 4.4-4.5 $mg/cm^3$.

The density of a humidified and/or compressed and rolled collagen carrier of the present invention is measured upon unrolling said rolled collagen carrier of the present invention. Please note that the density of a collagen carrier of the present invention is the density of the collagen carrier excluding the coating layer.

It is presently preferred to determine the density by weighing a collagen carrier of known volume, such as a rolled and/or compressed collagen carrier of a certain size (see the examples section), such as a large size collagen carrier (also called a strip or a fleece). The density is calculated by dividing the mass of the collagen carrier by the volume of the collagen carrier. The method and the equipment used for determining the density are disclosed in further detail in the example section below.

By the term "coating" is preferably meant a coating either comprising or essentially consisting of the biologically active substances fibrinogen and thrombin that are evenly distributed and fixed upon at least one side of a collagen carrier of the present invention, such as a rolled and/or compressed collagen carrier, such as an unrolled rolled and/or compressed collagen carrier. The coating may also include e.g. riboflavin (yellow color as marker of coated area). In one embodiment of the present invention, the active substances are preferably solid human fibrinogen, solid human thrombin and optionally solid riboflavin. Thus in one embodiment of the invention, the coating essentially consists of solid human fibrinogen, solid human thrombin and solid riboflavin. The coating is present on at least one side of the collagen carrier, such as a rolled and/or compressed collagen carrier, such as an unrolled rolled and/or compressed collagen carrier. Hence, in one embodiment the collagen carrier, such as a rolled and/or compressed collagen carrier, such as an unrolled rolled and/or compressed collagen carrier comprises one or more active sides wherein fibrinogen is present in an amount of 1.3-10 $mg/cm^2$, such as 2-10 $mg/cm^2$, such as 4.3-6.7 $mg/cm^2$, preferably about 3.6-7.4 $mg/cm^2$, such as about 5.5 $mg/cm^2$, and thrombin is present in an amount of 0.9-20 $IU/cm^2$, such as 0.9-15 $IU/cm^2$, such as 0.9-10 $IU/cm^2$, such as 1.0-5.5 $IU/cm^2$, preferably such as about 1.3-2.7 $IU/cm^2$, such as about 2.0 $IU/cm^2$. Said coating is preferably applied to at least one side of said collagen carrier, such as a rolled and/or compressed collagen carrier, such as an unrolled rolled and/or compressed collagen carrier.

When the collagen carrier, such as a rolled and/or compressed collagen carrier, such as an unrolled rolled and/or compressed collagen carrier, has a coating on one side of said carrier and when it is rolled the side coated with the biologically active substances can be externally oriented on said rolled collagen carrier, or the side coated with the biologically active substances can be internally oriented on the rolled collagen carrier. Presently, the first alternative is preferred for a rolled compressed collagen carrier of the present invention, i.e. external orientation of said coating.

By the term "diameter" of e.g. the rolled collagen carrier is meant the diameter of the cross section of any type of collagen carrier that has been rolled or coiled according to the present invention. Thus, the diameter of the resulting rolled collagen carrier as measured on the cross section (e.g. the shortest side) is about 5-12 mm, such as about 6-11, such as about 7-10 mm, such as about 8-9 mm, such as at the most 11 mm, preferably such as at the most 10 mm, preferably such as at the most 9 mm, such as at the most 8 mm, such as at the most 7 mm, such as at the most 6 mm, such as at the most 5 mm, such as at the most 4.5 mm, such as at the most 4 mm, such as at the most 3.5 mm, such as at the most 3 mm, such as at the most 2.5 mm, such as at the most 2.0 mm, such as at the most 1.5 mm, such as at the most 1.0 mm. The preferred diameter is less than 10 mm for midi sized fleeces, i.e. midi sized fleeces have the dimensions 46-49 mm*46-50 mm*4-7 mm. In FIG. 3 the length and width of a pre-rolled collagen carriers according to the invention is shown.

By the term "thickness" is meant the shortest measurable distance across any collagen carrier of the invention that is unrolled or nonrolled, which means that the thickness depends on whether the collagen carrier has been previously rolled or not and/or whether it has been previously compressed, humidified or not. When the term thickness is used to describe any type of unrolled or nonrolled collagen carrier according to the present invention the thickness is meant to mean the thickness which is about 1-10 mm, such as about 2-8, such as about 4-6, such as at the most 10 mm, such as at the most 9 mm, such as at the most 8 mm, such as at the most 7 mm, such as at the most 6 mm, such as at the most 5 mm, such as at the most 4 mm, such as at the most 3 mm, such as at the most 2 mm, such as at the most 1 mm. In an embodiment the preferred thickness of a collagen carrier is 4-7 mm. In another embodiment, the preferred thickness of an unrolled collagen carrier is at the most 4 mm.

By the term "sterility assurance level (SAL)" is meant a term used in microbiology to describe the probability of a single unit being non-sterile after it has been subjected to a sterilization process. For example, medical device manufacturers design their sterilization processes for an extremely low SAL leading to a $10^{-6}$ microbial survivor probability, i.e. assurance of less than or equal to 1 chance in 1 million that viable microorganisms are present in the sterilized device, as defined in USP 34<1211> (United States Pharmacopeia version 32, chapter 1211. SAL is also used to describe the killing efficacy of a sterilization process, where a very effective sterilization process has a very low SAL.

Sterilisation can occur before and/or after any packaging steps.

Gamma radiation can be used as a sterilization method to kill living organisms in a process called irradiation. Applications of irradiation include sterilizing medical equipment as an alternative to autoclaves or chemical means. In one embodiment of the present invention, a collagen carrier, such as a rolled and/or compressed collagen carrier, is subjected to gamma radiation. The gamma radiation may reduce the obtained PCT-value of the collagen carrier, such as no more than 0.5%, such as no more than 1%, such as no more than 2%, such as no more than 3%, such as no more than 4%, such as no more than 5%, such as no more than 6%, such as no more than 7%, such as no more than 8%, such as no more than 9%, such as preferably no more than 10%, such as no more than 11%, such as no more than 12%, such as no more than 13%, such as no more than 14%, such as no more than 15%, such as no more than 16%, such as no more than 17%, such as no more than 18%, such as no more than 19%, such as no more than 20%, such as no more than 25%. This was evaluated in vitro by visual inspection of adherence of a rolled collagen carrier according to the invention on liver tissue. Fibrinogen is preferably present in an amount of 2-10 $mg/cm^2$ and thrombin is preferably present in an amount of 1.0-5.5 $IU/cm^2$ after the irradiation process and it is preferred that the levels may exceed their respective levels such as no more than 0.5%, such as no more than 1%, such as no more than 2%, such as no more than 3%, such as no more than 4%, such as no more than 5%, such as no more than 6%, such as no more than 7%, such as no more than 8%, such as no more than 9%, such as preferably no more than 10%, such as no more than 11%, such as no more than 12%, such as no more than 13%, such as no more than 14%, such as no more than 15%, such as no more than 16%, such as no more than 17%, such as no more than 18%, such as no more than 19%, such as no more than 20%, such as no more than 25%. It is noted that "exceeding their respective levels" means that the values may either increase or decrease.

It is preferred that the rolled and/or compressed collagen carrier can be stored for an acceptable duration of time whilst maintaining their biological and physiochemical properties, i.e. preferably, storage neither affects the physical and chemical properties of said rolled and/or compressed collagen carrier nor the in vitro adherence (to liver tissue) and adhesive strength (PCT-value) of the rolled and/or compressed collagen carriers.

An acceptable shelf-life is preferably up to 60 months, such as up to 54 months, such as up to 48 months, such as up to 42 months, such as up to 36 months, such as up to 30 months, such as up to 24 months, such as up to 18 months, such as up to 12 months, such as up to 6 months, such as up to 5 months, such as up to 4 months, such as up to 3 months, such as up to 2 months, such as up to 1 month. Hence, it is preferred that rolled and/or compressed collagen carriers of the present invention are stable.

By the word "stable" is meant that said rolled and/or compressed collagen carriers are physiochemical and biologically stable meaning that they retain the same properties as they had when they were prepared. Hence, said rolled and/or compressed collagen carriers retain their stability under transport, warehousing (storage), logistics, sales, and up to and including the end use of said rolled and/or compressed collagen carriers i.e. the collagen carriers maintain regulations and all end-use requirements.

Silica gel is preferably used to mean a granular, vitreous, porous form of silicon dioxide made synthetically from sodium silicate. Silica gel is a commonly used desiccant as beads packed in a permeable bag.

It may happen that one or more solvents or moisture from the room (aqueous vapour) is absorbed passively by a collagen carrier, such as a rolled and/or compressed collagen carrier during processing. In one embodiments, if such passive absorption of moisture, such as water, has taken place a residual amount of said moisture is acceptable such as no more than 0.1% w/w, such as no more than 0.2% w/w, such as no more than 0.5% w/w, such as no more than 0.8% w/w such as no more than 1.0% w/w, such as no more than 1.2% w/w, such as no more than 1.4% w/w, such as no more than 1.6% w/w, such as no more than 1.8% w/w, such as no more than 2.0% w/w, such as no more than 2.5% w/w, such as no more than 3.0% w/w, such as no more than 3.5% w/w, such as no more than 4.0% w/w, preferably such as no more than 5.0% w/w, such as no more than 8.0% w/w, such as no more than 10.0% w/w, such as no more than 12.5% w/w, such as no more than 15.0% w/w, such as no more than 17.5% w/w, such as no more than 20.0% w/w, such as no more than 22.5% w/w, such as no more than 25.0% w/w, such as no more than 27.5% w/w, such as no more than 30.0% w/w, such as no more than 32.5% w/w, such as no more than 35.0% w/w. When the passively absorbed solvent is water no more than 8.0% w/w residual water is preferred, preferably such as no more than 5.0% w/w. Residual solvent is measured by conventional methods known to the person skilled in the art, such as by using gas chromatography (GC). GC is a common type of chromatography used in analytical chemistry for separating and analyzing compounds that can be vaporized without decomposition. In the present invention, GC is used to determine one or more solvents or moisture from the room (aqueous vapour) in the collagen carrier.

By the term "sterilizing" is meant any well known method of sterilizing an object such as in the present invention a collagen carrier, such as a rolled and/or compressed collagen carrier. Any such appropriate sterilization method should result in the required probability of a single unit being non-sterile after it has been subjected to the sterilization process. Hence, preferably not more than one collagen carrier, such as a rolled and/or compressed collagen carrier in a million should be nonsterile after the sterilization process. An example of a sterilization process is gamma radiation. Sterilization can also be achieved by applying the proper combinations of heat, chemicals, irradiation, and high pressure, but these are less preferred methods. In a preferred embodiment the sterilization is performed using gamma irradiation.

In an embodiment package testing is conducted and documented to ensure that packages meet regulations and all end-use requirements. Manufacturing processes are controlled and validated to ensure consistent performance.

Preferably, a suitable container of the present invention is sterilized in the package. Medical device packaging is highly regulated and the sterility must be maintained throughout distribution to allow immediate use by physicians. A series of special packaging tests is well known in the art and used to measure the ability of the package to maintain sterility. Relevant standards include: ASTM D1585—Guide for Integrity Testing of Porous Medical Packages, ASTM F2097—Standard Guide for Design and Evaluation of Primary Flexible Packaging for Medical Products, EN 868 Packaging materials and systems for medical devices which are to be sterilized. General requirements and test methods, ISO 11607 Packaging for terminally sterilized medical devices, and others.

In an embodiment the first and/or second container is a foil packaging material, such as a single or double aluminium foil or a plastic packaging material, such as a polystyrene or PET (polyethylene terephthalate) or a combination of a foil and plastic packaging material, such as a single or double aluminium foil and as a polystyrene or PET (polyethylene terephthalate).

By the term "weight-weight percentage" or "% w/w" is meant grams substance per grams of another substance in percent (per 100 gram). Thus, if e.g. residual water is present in an amount of 2% w/w in a collagen carrier, it is meant to mean 2 grams of water is present with 98 grams of collagen carrier. The total weight will be 100 grams of the collagen carrier including the residual water but the volume of the 100 grams of residual may be different from 100 ml.

Note that by the "weight" of the collagen carriers is meant the weight of the collagen carrier excluding the weight of the coating layer.

It should be noted that embodiments and features described in the context of one of the aspects of the present invention also apply to the other aspects of the invention i.e. all aspects relating to a rolled compressed collagen carrier also apply to a compressed collagen carrier or a rolled collagen carrier or an unrolled rolled compressed collagen carrier or a coiled collagen carrier (as the terms "coiled" and "rolled" are used interchangeably herein), and similarly for the process aspects.

The coiled collagen carrier comprises a collagen layer. The collagen layer can be made from any suitable collagen, such as e.g. a collagen foam or sponge, such as e.g. the commercially available Nycomed "TachoTop" product. A preferred collagen type is human collagen, such as a solidified human collagen foam. The coiled collagen carrier also comprises a coating layer on top of the collagen layer, which comprises thrombin and fibrinogen. The thrombin is preferably mostly solid or solid. The fibrinogen is preferably mostly solid or solid. Preferably both the thrombin and fibrinogen are solid. Preferably the coating also comprises riboflavin, which provides a yellow colour and enables the medical practitioner to determine which side of the collagen carrier is the active side.

In preferred embodiments of the present invention, at least the outer windings or each winding of the coiled collagen carrier is orientated so that the coating layer constitutes the inner surface of each winding. In other embodiments of the present invention, each winding or at least the outer windings of the coiled collagen carrier is/are orientated so that the coating layer constitutes the outer surface of each of said windings.

In an embodiment of the present invention, the collagen carrier is preferably a layered construction, for example consisting of a layer of collagen and a coating layer on top of the collagen layer.

The coiled collagen carrier of the present invention is form-stable. This can for example mean that the coiled collagen carrier is form-stable in the sense that it does not un-coil "when at rest". In one embodiment of the present invention, the form-stability of the coiled collagen carrier diminishes when moisture is applied to it by which is meant that the product becomes more flexible (i.e. less form-stable). In a preferred embodiment of the present invention, the form-stability of the coiled collagen carrier is provided substantially only by the coating. At least some of the form-stability of the coiled collagen carrier can in one embodiment be provided by the outer most winding of the carrier. In one embodiment of the present invention, the form-stability of the coiled collagen carrier is provided by a region at the edge of the coiled collagen carrier adhering to the subjacent winding. In another embodiment, the form-stability of the coiled collagen carrier is provided by an adherence between the windings. In an embodiment of the present invention, the form-stability of the coiled collagen carrier is provided by the coiled collagen carrier having no mechanical tension. In an embodiment of the present invention, the form-stability of the coiled collagen carrier is provided by outbalancing mechanical tension acting to un-coil the coiled collagen carrier by an adherence between the windings. In an embodiment of the present invention, the form-stability of the coiled collagen carrier is provided by the coil having a elasticity module of 5-100 N/cm$^2$.

In one embodiment of the present invention, the form-stability is provided by the coiled collagen carrier forming a brittle coil which, when subjected to stress, breaks without significant deformation.

In a preferred embodiment of the present invention, the coiled collagen carrier in an unrolled configuration is a (preferably rectangular or square-shaped) sheet, preferably having a width, a length and a thickness. Preferably, said unrolled collagen carrier is a rectangular or square sheet. Preferably the sheet has a thickness of between 0.5 mm and 10 mm, such as e.g. 0.5-8 mm, for example 0.5-6 mm. In a preferred embodiment of the present invention, said thickness is preferably 1-4 mm. such as preferably 1-3 mm. The thickness can in one embodiment be at the most 4 mm, or at the most 5 mm, or at the most 6 mm, or at the most 7 mm. The unrolled collagen carrier preferably has a surface area on its top surface (which preferably is coated with the coated layer) of 4-100 cm$^2$, more preferably 5-75 cm$^2$, such as 10-50 cm$^2$, such as e.g. 20-30 cm$^2$, for example 25 cm$^2$ which can e.g. be given by a top surface of a 5 cm×5 cm square collagen sheet.

In an embodiment of the present invention, the coiled collagen carrier comprises or consists of three, four or five windings.

In an embodiment of the present invention, the coiled collagen carrier has a cylindrical shape with an outer diameter of less than 12 mm, such as less than 11 mm, such as less than 10 mm, such as less than 9 mm, such as less than 8 mm, such as less than 7 mm, such as less than 6 mm, such as less than 5 mm, such as less than 4 mm, such as less than 3 mm. For example, the coiled collagen carrier has an outer diameter of 1-12 mm, such as e.g. 3-11 mm, such as e.g. 5-10 mm, such as preferably 5-9 mm, such as e.g. 6-8 mm.

In an embodiment of the present invention, the coiled collagen carrier has an s-shaped inner most winding about the longitudinal axis of the coiled collagen carrier.

It is preferred that the coating of the coiled collagen carrier coating layer has no through-going cracks, such as through-going cracks visible by the naked eye.

The present invention further relates to a packed coiled collagen carrier, comprising the coiled collagen carrier according to the present invention arranged in a container. The container can for example be sealed to prevent contamination and/or degradation and/or to maintain form-stability of the coiled collagen carrier. Preferably the container is sealed to prevent contamination and/or absorption of liquid solvents such as e.g. water. The container can in one embodiment further comprise a desiccant, such as silica gel, arranged in the container.

The container can in an embodiment comprise an inner container (a container part with cover) and an outer container (a second container). In some preferred embodiments, the inner container comprises a compartment in the form of a cavity shaped as a segment of a cylinder, and wherein the curved part of the cylinder segment extends at least 180°, the compartment being sealed by cover preferably being a tear-off or breakable foil. It is preferred that the outer container comprises a sealed pouch inside which the sealed inner container is arranged together with a desiccant.

The packed coiled collagen carrier according to the invention can also further comprise a label arranged to be visually inspected without opening the package and indicating whether the package with coiled collagen carrier has been exposed to radiation sterilization, such as to X-rays, such as to high-energy X-rays, or such as to gamma radiation, or such as to electron beams, or such as to ultraviolet light. The label can for example be arranged on the outside of the outer container.

The packed coiled collagen carrier according to the invention can also comprise a sterile plastic bag with a minimal amount of air inside, preferably with no air being in the bag, the bag being especially suited for protecting the coiled collagen carrier from being activated by bodily fluids when using it in e.g. surgery. This thin plastic bag may optionally be used after having un-packed the packed coiled collagen carrier according to the invention, for example by delivering the bagged collagen carrier to a site in the patient's body and then removing the plastic bag before uncoiling the collagen carrier.

An embodiment of the invention relates to a process according to the invention, wherein said collagen carrier has a density in the range of 3.0-4.5 mg/cm$^3$. Please note that the density of a collagen carrier of the present invention is the density of the collagen carrier excluding the coating layer.

It should be noted that embodiments and features described in the context of one of the aspects of the present invention also apply to the other aspects of the invention i.e. all aspects relating to a rolled compressed collagen carrier also apply to a compressed collagen carrier, or a rolled collagen carrier, or an unrolled rolled compressed collagen carrier.

All patent and non-patent references cited in the present application, are hereby incorporated by reference in their entirety.

A further aspect of the present invention relates to a bag or pouch comprising or consisting of one or more water-proof materials(s), said bag containing the rolled collagen carrier of the present invention. Thus, the present invention further relates to a bag or pouch comprising or consisting of one or more waterproof materials(s), said bag containing a coiled collagen carrier which comprises a collagen layer and a coating layer on top of the collagen layer, said coating layer comprising thrombin and fibrinogen, wherein said coiled collagen carrier has the shape of an elongated element with a number of windings of the collagen carrier about the longitudinal axis of the elongated element and at least one outer winding(s) of the carrier being orientated so that the coating layer constitutes the outer surface of each of said outer winding(s), wherein said coiled collagen carrier is form-stable and defines a collagen carrier in a coiled configuration where said outer winding(s) proceed along a spiral in a cross section of the collagen carrier. The bag or pouch is preferably sterile.

Examples of waterproof materials suitable for use in the present invention are one or more plastics (such as e.g. pvc and/or an x-ray detectable plastic) and/or flexible foils, such as aluminium foil. The material should be flexible to allow easy manipulation in the form of a bag or pouch.

Production of a Coiled Collagen Carrier.

A coiled collagen carrier may be produced by the following process. A collagen carrier as described herein is humidified by applying a solvent—typically being ethanol—to the coating of the collagen carrier. This humidification will soften the coating and as the collagen carrier is flexible in without being humidified, the humidified collagen carrier may be coiled. However, it has been found that it may be beneficial for the process to compress the humidified collagen carrier prior to coiling and if that is implement, the compression can be carried out by passing the humidified collagen carrier through the gap between a pair of rollers (the gap being smaller than the thickness of the humidified collagen carrier.

Coiling is typically performed by a coiling device comprising rotatable gripping means (typically embodied as a pair of tweezers or pincers) for gripping the collagen carrier along an edge and coiling the collagen carrier, and a support device supporting the collagen carrier while being coiled.

The supporting device may be formed as an open channel formed cavity through an end of which the rotatable gripping means extends during coiling.

After coiling the rotatable gripping means is extracted and the coiled collagen carrier is dryid to remove excess of solvent. When the coiled collagen carrier is dry the collagen carrier is form-stable and may be removed safely from the supporting device.

An example of an apparatus for providing coiled collagen carriers is shown in FIG. 8. The apparatus comprising a number of elements as shown in the figure and comprises in particular a device for applying moisture 40 to a collagen carrier 16 prior to coiling of a collagen carrier as disclosed herein.

The device for applying moisture 4 comprising a spray nozzle 42 directed towards the surface 41 of the coating layer of the collagen carrier, the spray nozzle 42 provides droplets as a mist or a spray of solvent. In the spray nozzle 42, droplets are produced assisted by sterile air, thereby ethanol is mixed with sterile air.

Thus, the collagen carrier is orientated with its coating surface facing upwardly towards the spray nozzle 42. The solvent penetrates into the coating of the collagen carrier and softens the coating of the collagen carrier 41. It has been found that, it can be sufficient to humidify only the coating layer or an upper part thereof of the collagen carrier, although it is also possible to humidify the whole collagen carrier.

The collagen carrier is conveyed by a conveyer belt 51 past the spray nozzle 42.

The apparatus 48 further comprises a coiling device 43, which is adapted to grip the moisturised collagen carrier along an edge and coil it into a coiled collagen carrier 16. The coiling device 43 comprises rotatable gripping means 44 for gripping the collagen carrier along an edge 45 of the collagen carrier and coil the collagen carrier by rotation of the gripping means 44 around an axis being parallel to the longitudinal extension of the gripping means 44.

Gripping along the edge 45 and rotating the gripping means 43 allows coiling of the collagen carrier into a desired shape, preferably with the collagen carrier being supported during coiling. To assure coiling and assist in defining the shape of the coiled collagen carrier 16, the coiling device 43 further comprises a support device 46 supporting the collagen carrier while being coiled. The support device 43 is typically a cavity arranged relatively to the gripping means 44 so that the surface of the support device 46 acts as counter pressure means by at least a part of the collagen carrier abutting at least a part of the inner surface of the cavity during coiling. As mentioned, the shape of the surface of the support device 46 at least assists in defining the shape of the coiled collagen carrier 16.

The gripping device 44 comprises a pair of elongated members 47, such as a pair of tweezers or pincers. The elongated members 47 has a longitudinal extension matching the width of the collagen carrier—the width of the collagen carrier is considered to be the dimension parallel to the extension of the elongated members 47—whereby the collagen carrier is gripped at the edge along the whole width by the elongated members 47.

Gripping of the collagen carrier is accomplished by decreasing the distance between the two elongated members 47 once the collagen carrier is located in between the elongated members 47 to an extent providing a gripping being sufficient to provide coiling once the elongated members 47 are rotated.

As shown in FIG. 8, the support device 46 is a cavity comprising a bottom part shaped as a segment of a cylinder having at least one open end through which the elongated members extend, and wherein the curved part of the cylinder segment extends at least 180°—in the embodiment shown in FIG. 8, the cylinder segments extends 180°. Thus, in the embodiment of FIG. 8, the cavity is channel-formed with two parallel side walls 8a extending from the bottom. This configuration of the cavity provides the channel with a generally "U"-shaped cross section, the bottom forming the curved part of the "U"-shaped cross-section and each side walls 8a forming the straight parts of the "U"-shaped cross section.

The elongated members 47 of the gripping device 44 extend into the cavity of the support device 8 through the open end. The elongated members 47 are furthermore extractable so that once the collagen carrier has been coiled and is located in the cavity of the support device 46 so that the end 52 of the collagen carrier is abutting the wall of the cavity of the support device, the elongated members 47 are extracted from the coiled collagen carrier 16. The elongated members 47 are extracted in a direction being parallel to the longitudinal extension of members. When another collagen carrier is to be coiled, the elongated members 47 are introduced back into the cavity of the support device 46 by moving the elongated members 47 in the opposite direction than during the extraction. Furthermore, the elongated members 47 are opened, that is the gap between the two members is larger than the thickness of a humidified and compressed collagen carrier so that the elongate members 9 are ready to receive a collagen carrier in between them. By extractable is preferably meant that elongated members 9 can be removed from coiled collagen carrier after the coiling has been performed and in general also that they can be removed from the position where coiling is performed. Thus, the extractable is considered to cover also re-tractable.

Thus, the apparatus of FIG. 8 is adapted to move the pair of elongated members 47 in a reciprocating movement, so that the elongated members can be retracted after the collagen carrier has been coiled.

The apparatus 48 further comprises a compressing device. The compressing device being arranged to compress the moisturised collagen carrier prior to coiling of the moisturised collagen carrier, that is as indicated in FIG. 8, the compressing device being arranged after the device for applying moisture 40 and before the coiling device 43.

The compressing device comprises a pair of rollers 50 having a gap size being smaller than the thickness of the collagen carrier before passing through the set of rollers 50 and being arranged to compress the moisturised collagen carrier prior to coiling of the moisturised collagen carrier. The compression being provided because the gap in between the rollers is smaller than the thickness of the moisturised collagen carrier. As indicated in FIG. 8, the rollers 50 rotate in opposite directions so as to transport the collagen carrier through the pair of rollers 50 towards the coiling device 43.

The gap size between the rollers is selected so as to provide the desired compression ratio. Typically and preferred numbers for the gap size is no more than 0.5, preferably no more than 0.6 or between 0.5-1.0 mm, or no more than 0.75 mm. However, the gap size should be selected in accordance with the thickness of the collagen carrier 3 so as to obtain the desired compression ratio.

An example of a form-stable coiled collagen carrier is shown in FIG. 7, in which figure the form-stable coiled collagen carrier is located in the compartment of the container part.

BRIEF DESCRIPTION OF THE FIGURES

The invention and in particular preferred embodiments thereof will now be described in more detail with regard to the accompanying figures. The figures show ways of implementing the present invention and are not to be construed as being limiting to other possible embodiments falling within the scope of the attached claim set.

FIG. 4 shows schematically and in a three dimensional view a packaging according to the present invention which further comprises a second container inside which the container part of FIGS. 1 and 2 with coiled collagen carrier is arranged.

DETAILED DESCRIPTION OF PREFERRED EMBODIMENTS

Figure 1:
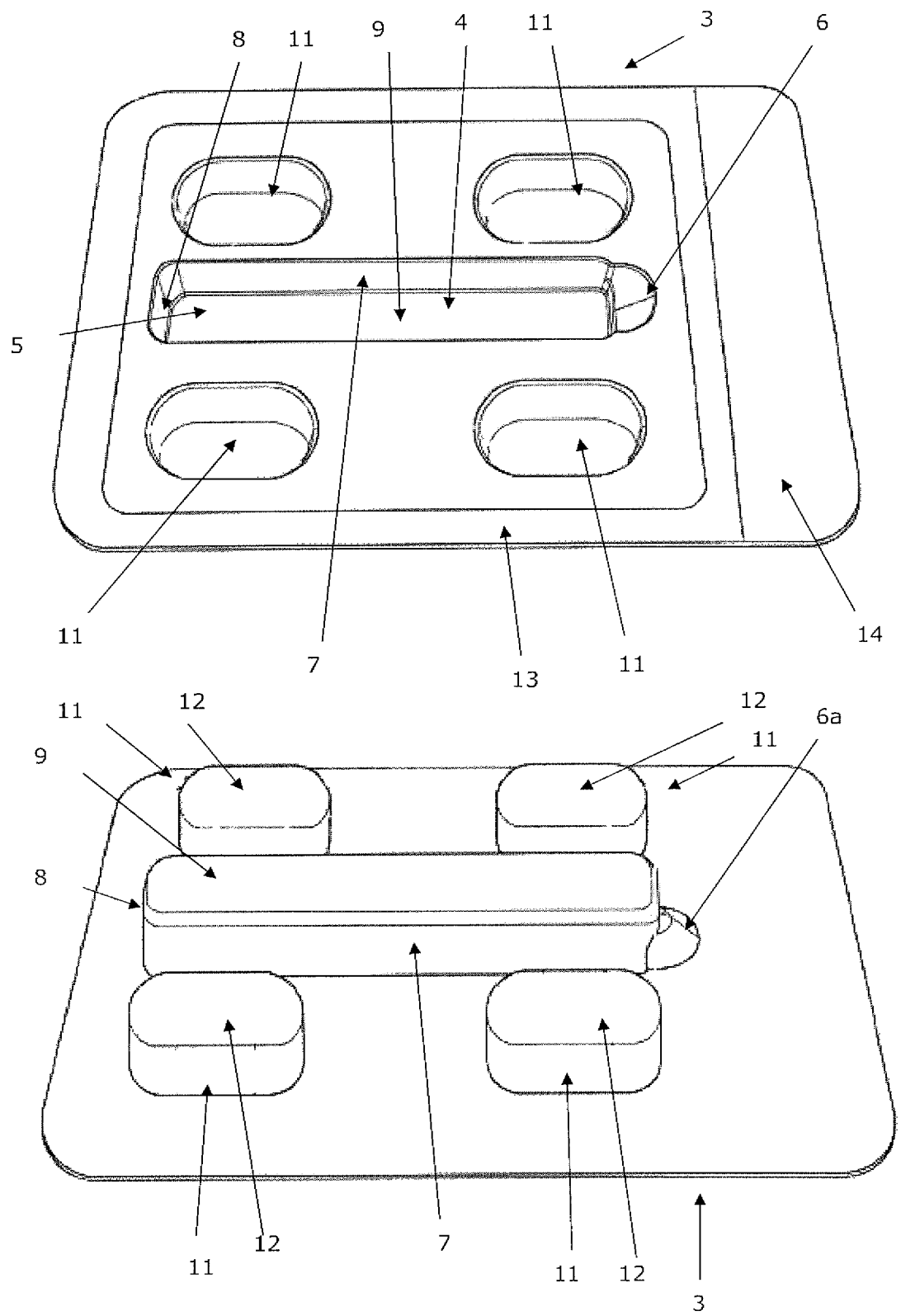
FIG. 1 shows schematically and in a three dimension view a container part of a packaging for storing a form-stable coiled collagen carrier according to preferred embodiment of the invention; upper part of FIG. 1 shows the container part as seen oblique from above, lower part of FIG. 1 shows the container part as seen oblique from below.

With reference to the accompanying figures, a packaging 1 for storing a form-stable coiled collagen carrier 16 will now be presented. Reference is made to FIG. 1 which shows a container part 3 of a packaging 1 according to the invention as seen oblique from above in the upper part FIG. 1 and as seen oblique from below in the lower part of FIG. 1.

A packaging according to the invention stores a form-stable coiled collaged carrier 2 in a compartment 4 which, as will be disclosed in further details below, is closed by a cover. Such form-stable coiled collagen carriers comprises a collagen layer and a coating layer comprising thrombin and fibrinogen and having the shape of an elongated element with a number of windings of the collagen carrier about the longitudinal axis of the elongated element with at least one outer winding(s) being orientated so that the coating layer constitutes the outer surface of each of said outer winding(s).

Figure 7:
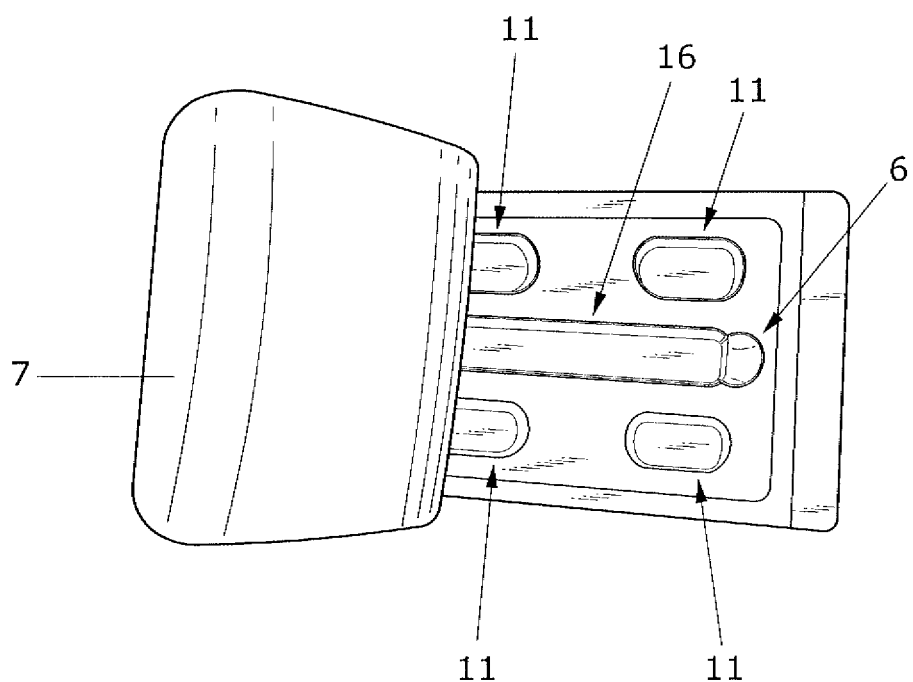
FIG. 7 shows a photograph of the container part containing a form-stable coiled collagen carrier and the cover being partly removed.
Figure 8:
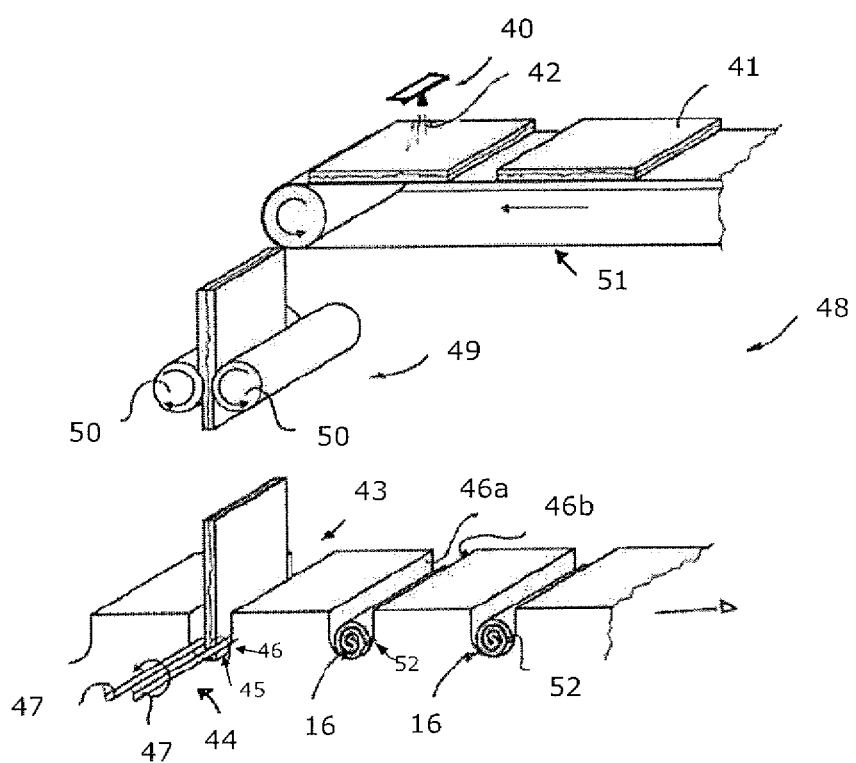
FIG. 8 shows schematically a preferred embodiment of an apparatus for providing a coiled collagen carrier according to the present invention.

As disclosed in FIG. 1, the packaging 1 comprises a container part 3 which has a compartment 4 in which at least a part of the coiled collagen carrier 16 is contained (the coiled collagen carrier is not shown in FIG. 1 for clarity reasons only). In many of the preferred embodiments, the coiled collaged carrier 16 is fully contained in the compartment 4 which means that no part of the collagen carrier 16 extends out of the compartment 4. FIG. 7 which is a photograph of the container part 3 and the cover 7 partially removed shows a form-stable coiled collagen carrier 16 arranged fully in the compartment 4.

The compartment 4 is an open-ended compartment in the sense that it has an opening 5 which is provided in an upper surface 14 of the container part 3. The opening 5 is preferably considered to be the two-dimensional plane extending across the compartment 4 in the plane of the upper surface 14. The extremity of the opening is called the rim of opening 5.

As also shown in FIG. 1, the container part 3 comprises at least one cavity 6. The cavity 6 is designed to get easy access to the coiled collagen carrier 16 contained in the compartment 4 as it serves as a passage for a fingertip or tool allowing the fingertip or tool to gain access to the coiled collage carrier 16. It is noted that the size of the compartment 4 relative to the size of the coiled collagen carrier 16 is often chosen so that the coiled collage carrier fits rather snug into the compartment (to minimise the risk of breakage due to e.g. sliding movements of the coiled collagen carrier relative to the compartment). So in some embodiments the opening is not more than 0.5-5 mm wider and not more than 0.5-5 mm longer than the collagen carrier, such as not more than 2 mm wider and not more than 2 mm longer than the collagen carrier.

The opening 5 is preferably considered not to extend over the cavity 6 and the rim of the opening 5 is therefore preferably considered to be the projection of the outermost extensions of the compartment 4 onto a plane defined by the plane of the upper surface 14. In regions where no cavity is present, the rim thereby coincides with the edge between the compartment 4 and the upper surface 14. In regions where a cavity is present, the edge between the upper surface 14 and the compartment 4 is not present and the rim is preferably considered to be the line connecting the rim on both sides of the cavity 6. With reference to e.g. FIG. 3, the rim is coinciding with the outer edge of the region shown with the width 11.4 mm and length 60 mm.

The cavity 6 is in the embodiment shown in FIG. 1 situated at the rim of the opening 5, wherein said cavity 6 opens into the compartment 4 and into the upper surface 14. Thereby, the coiled collagen carrier may be lifted or in general manoeuvred out of the compartment by positioning a fingertip or a tool (such as a grasper) in the cavity 6 and while abutting or gripping the end of the coiled collagen carrier the coiled collagen carrier may be angled or lifted out of the compartment 4.

Figure 3:
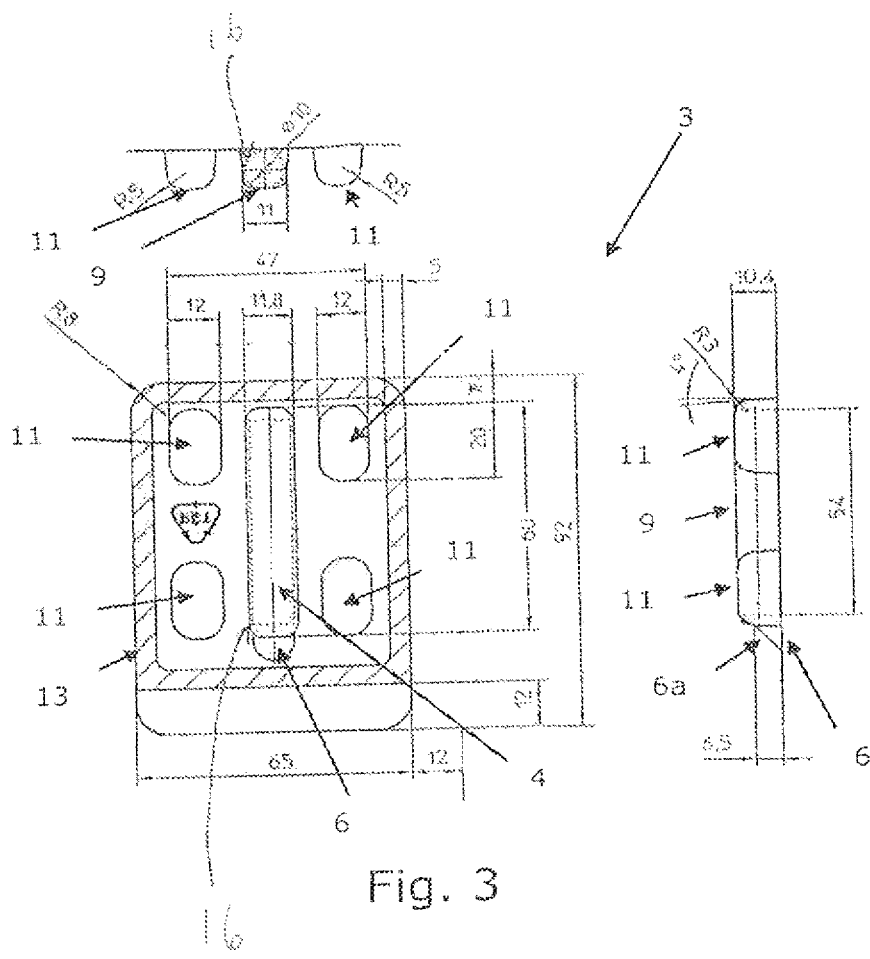
FIG. 3 shows the container part of FIG. 1 in an orthographic projection, the label "PET" is embossed into the surface, the cross hatched region indicates the region where the cover is heat-welded to the upper surface of the container part; the dotted lines shown in the compartment indicates the position of the coiled collagen carrier.

In order for the opening 5 to allow placement in the compartment 4 of the coiled collagen carrier typically having the shape of a substantially cylindrical element with a diameter and a length, the opening 5 is generally rectangular shaped, and the length and the width of the opening are larger than the respective length and the diameter of the coiled collagen carrier. Preferred dimensions for a container part 3 adapted to store a form-stable coiled collagen carrier with a diameter of 10 mm and an length in the order of 55 mm are shown in FIG. 3 where all the numbers are in mm. The thickness of the sheet material from which the container part 3 is made from is 0.5 mm In the embodiment shown in FIG. 1, the compartment is substantially cuboid-shaped having a length, a width and a depth. It is noted, that "cuboid" is used in a broad sense including geometries where the length, width and depth are (as shown in FIG. 1) not equal. The depth being measured from the opening 5 and to the bottom of the compartment 4, the length being the longer of the length and the width. By substantially cuboid is preferably meant that the edges and corners of the compartment 4 are rounded and that the wall sections of the compartment 4 may be sloping. In the latter case, the compartment may be shaped as a frustum of a pyramid. However, it is generally preferred that the walls of the compartment are vertical—this can be more easily seen in FIG. 3

In the embodiment shown in FIG. 1, a cavity 6 is situated at one of the shorter sides of the opening 5, that is at an end of the compartment 4. However, further cavities 6 may be present and/or the position of the cavity/cavities 6 may be selected according to certain requirements. For instance, two cavities 6 may be present, one being arranged at end of the compartment 4, which will allow access to the coiled collagen carrier at both ends.

Furthermore, a cavity 6 may be situated at one or both of the longer sides of the opening 5. Cavities 6 situated along the longer sides of the opening 5 are preferably arranged at the middle of the longer sides so as to allow access of the coiled collaged carrier at its middle.

The cavity extends from the upper surface 14 and opens into the compartment 4. Accordingly, the cavity 6 comprises a wall or at least a wall section 6a extending from a position at the upper surface 14 outside the rim of the opening 5 and towards the bottom of the compartment 4. The position from where the wall or wall section of the cavity 6 extends is in the embodiment shown in FIG. 1 the edge between the cavity 6 and the upper surface 14. The wall or wall section extends sufficiently far down towards the bottom of the compartment to allow access to the coiled collaged carrier, which often means at least half-way down the height of the compartment 4. In FIG. 1, the wall extends a distance h being 60% of the depth d (including the thickness of the bottom) of the compartment 4. As also disclosed in FIG. 1, the wall or wall section of the cavity 6 extends sloped (see also the side view of FIG. 3). However, the wall or wall section may extend in a curved fashion, such as extending along a curve having a radius of curvature.

As also shown in FIG. 1, the edge formed between the cavity 6 and the upper surface 14 of the container part 3 extends along a section of an ellipse. Although this may be preferred, the edge may extend in other ways. In the embodiments shown in FIG. 1 the cavity 6 is formed as a segment of a cylinder.

Figure 2:
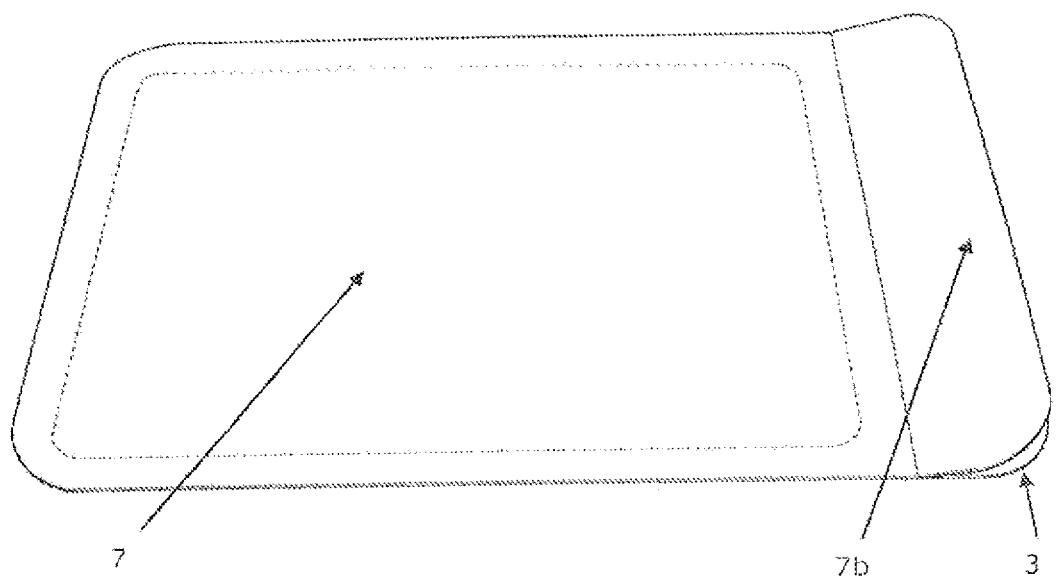
FIG. 2 shows schematically and in a three dimensional view a cover for the container part shown in FIG. 1 according to a preferred embodiment of the invention the cover is shown applied to the container part and oblique from above.

The packaging further comprises a cover 7 (see FIG. 2) covering the opening 5 of the packaging. The cover has as indicated in FIG. 2 a shape coinciding with the upper surface 14 of the container part 3 and does therefore extend across the whole upper surface 14 of the container part 3 when attached to the container part 3. However, the cover may have a shape so that it only covers the opening 5 and the cavity 6.

The cover 7 is attached to the container part 3 in a manner allowing manual removal of the cover 7. By manual removal is preferably meant that the cover may be removed by use of fingers and preferably not by use of tools.

Accordingly, the cover 7 is attached by a heat welding or a gluing to the upper surface 14 of the container part 3. In the embodiment shown in FIG. 1, the cover 7 is attached by heat welding.

The cover 7 is in the embodiment shown in FIG. 1 attached to the container part 3 along an outer rim 13 of the container part 3 encircling the opening 5 and the cavity 6 as well as the opening of the downwardly protruding supporting elements 11. In FIG. 1, the heat welding is shown by the cross hatching 15 along the outer rim 13.

As shown in FIG. 1, the heat welding provides a section 17, where the cover 7 is not attached to the container part 3. This part of the cover is labelled 7b in FIG. 2 and serves as a pull-tab 7b not being attached to the container part 3. Upon removal of the cover, a person may grip the pull-tab by his fingers (or a tool) and pull in cover 7. Counter acting this pulling motion by fixating or holding (e.g. by use of his fingers or a tool) the container part 3, the heat welding will gradually break whereby the cover 7 is removed from the container part 3.

After coiling, the coiled collagen carrier may contain moisture (solvent, such as ethanol, isopropanol and/or water) and it is often desirable to allow such moisture to escape the coiled collagen carrier after it has been arranged in the compartment 4 and the cover 7 has been applied to the container part 3. To accomplish this, the cover 7 is preferably made from a permeable material allowing gas and/or liquid to permeate through the cover.

Often the cover is made from the material Tyvek® made by DuPont™ (further details are provided below on the material), i.e. medical grade high density polyethylene foil. The thickness of the cover is typically 0.25 mm The packaging shown in FIG. 1 is made from a sheet of material having a thickness being at least 50 times smaller than the longitudinal extension of the container part (92 mm—see FIG. 3). Accordingly, the container part 3 is considered to be sheet-shaped. The compartment 4 and the cavity 6 are formed as indentations in the sheet.

The container part 3 of the packaging shown in FIG. 1 is made from plastic, such as Polyethylene terephthalate (PET) (further details pertaining to the material of the packaging are described above and below), and the container part 3 is thermoformed by e.g. injection moulding, blow moulding, vacuum moulding or rotational moulding.

The upper surface 14 of the container part 3 is said to be horizontal. It is noted that horizontal is used relatively to the orientation of the FIG. 1 and is not to be construed limiting as to be aligned with the horizon. In line therewith, the compartment 4 is cuboid shaped and comprises a horizontal bottom 9, two side walls 7 and an end wall 8 as shown in FIG. 1. The two side walls 7 and the end wall 8 may be inclined with respect to vertical whereby the compartment 4 has the shape of a frustum of a pyramid. However, in the embodiment shown in FIG. 1, the side walls 7 and the end wall 8 are substantially vertically extending walls. A small deviation from vertical may be desired to allow easy removal from a mould used during production of the container part 3.

The intersections of the bottom 9 with the side walls 7 and the end wall 8 respectively are rounded in the embodiment of FIG. 1. This may be provided inter alia to allow easy removal from a mould during production and/or to provide an accommodation of the coiled collagen carrier reflecting the substantial cylindrical shape of the coiled collagen carrier, which may provide a more safe storage of the coiled collagen carrier with less risk of destruction due to e.g. handling of the container 3 with cover 7.

As disclosed above, the cavity 6 typically extends from the horizontal level of the upper surface 14 and towards the bottom of the compartment 4, such as less than half-way down or at least half-way down the height of the compartment. In some embodiments, the cavity 6 extends all the way to the bottom of the compartment 4.

As indicated above, the cover 7 is made from a permeable material allowing substances to permeating through the cover 7. In order to seal the coiled collagen carrier and store it in a controlled atmosphere, the packaging 1 further comprises a second container 10 (see FIG. 4) inside which the container part 3 with coiled collagen carrier and the cover 7 is arranged (see FIG. 6).

Figure 4A:
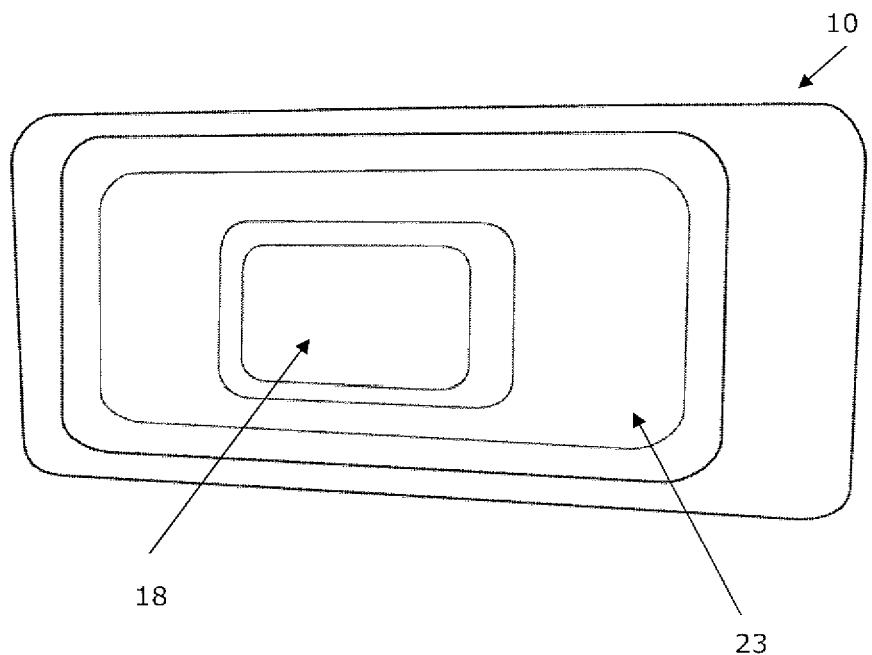
FIG. 4a shows the exterior of the second container in a sealed state and FIG. 4b shows the interior of the second container in a opened state with the container part and cover shown in FIGS. 1 and 2 removed for clarity reasons only (the second container shown is adapted to house the container part with cover as shown in FIGS. 1 and 2 although it may house a container part with cover being longer than the once shown in FIGS. 1 and 2—this applies to FIGS. 5 and 6 also)
Figure 4B:
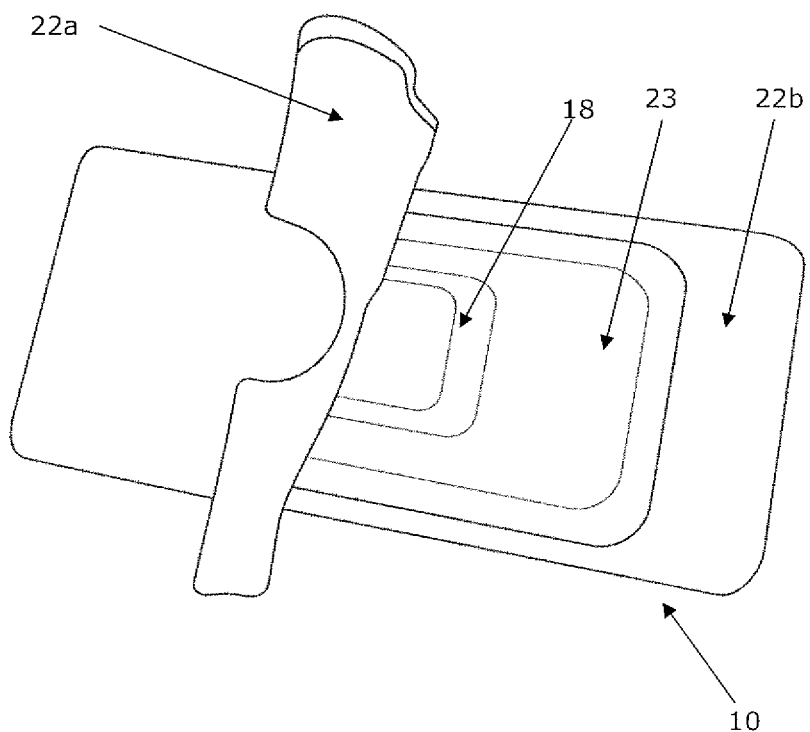
Figure 5:
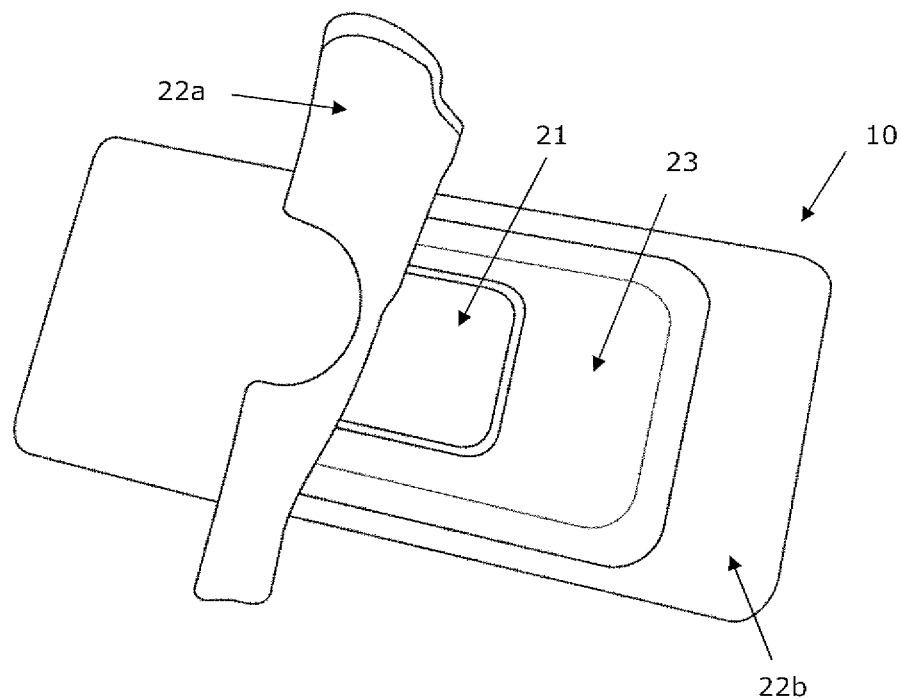
FIG. 5 shows schematically and in a three dimensional view the second container with the desiccant present in a depression.
Figure 6:
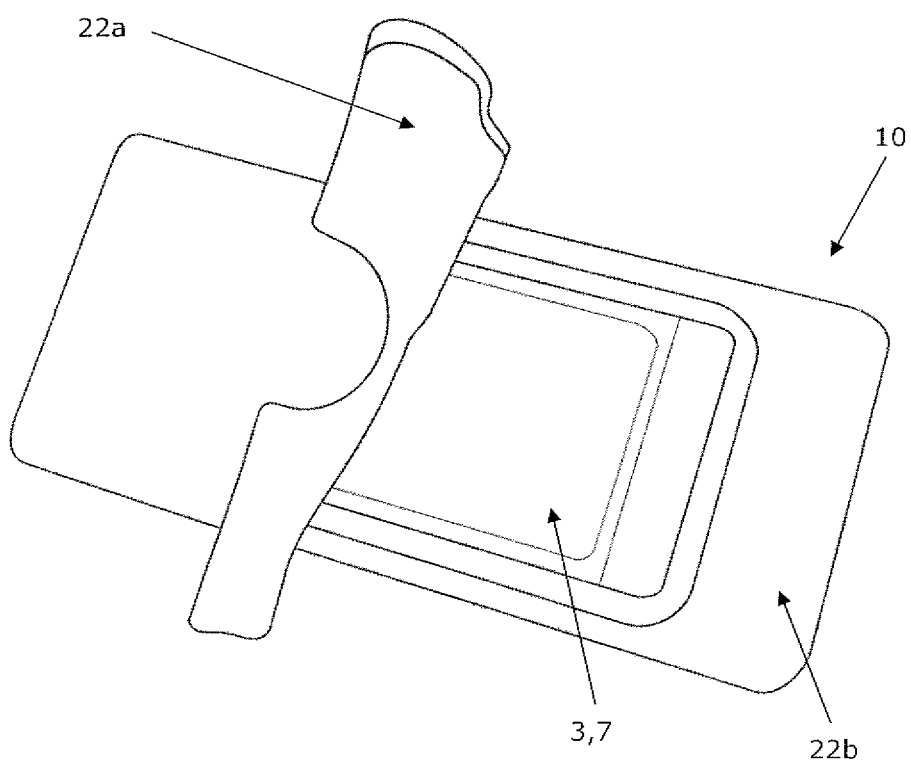
FIG. 6 shows schematically and in a three dimensional view the second container with the container part and cover present.

Referring to FIG. 4-6, the second container 10 is made from a fluid tight material and is fluid-tight when closed. It is further noticed that the container shown in FIG. 4a is disclosed in its condition when it leaves the production line and has no wrinkles. The container disclosed in 4b, 5 and 6 shows some wrinkles due to the manual handling of the container.

The second container 10 is in the embodiments of FIGS. 4-6 formed by two sheet of materials being glued or heat welded together at the rims of the sheets in a manner providing pull-tabs 22a and 22b used pull the second container open. Alternatively the second container 10 may be formed by a single sheet which is folded and glued or heat welded together after folding. The second container also comprises a compartment 23 adapted to house the container part 3 with cover 7.

The packaging shown in FIG. 4 comprises a desiccant 21 arranged inside the second container 10 and outside the container part 3 with coiled collagen carrier and the cover 7. In the embodiments shown in FIG. 3, the desiccant 21 is arranged in the depression 18 (when viewed from the inside the second container 10 as shown in fig. bb) provided in the compartment 23 of the second container 10.

The desiccant preferably comprises a drying agent being an orange gel, in granulate form with a granulate size ranging between 0.2 mm-1.5 mm of amorphous silica with ferric. The composition is Synthetic amorphous silica>93 w/w %, Ferric ammonium sulphate<5 w/w %, water<5 w/w %. The drying agent is arranged in a bag made of permeable material, such as Tyvek® with welded seam.

The second container 10 of FIGS. 4-6 is said to be in the form of a pouch inside which the container part 3 with coiled collagen carrier and the cover 7 and the desiccant are arranged. Due to pull-tabs and the strength of gluing or welding used to form the pouch, the pouch is tear-openable or pull-openable.

The second container 10 shown in FIGS. 4-6 is made from a foil comprising or consisting of aluminium, and made by punching out sheets from a reel of foil whereafter the second container is welded or glued. The thickness of the foil is 0.25 mm In a particular preferred embodiment, the outer container 10 is made from aluminium laminated foil PA25/AL 45/PE 40, with the following composition:

| | |
|---|---|
| OPA foil, oriented polyamide foil, nylon 6 | 25.0 μm |
| Adhesive (AD2746), Polyurethane basis | 3 g/m² |
| Lacquer, golden (outer side) | 2 g/m² |
| Aluminium strip, AL 98.6 | 45 μm |
| Adhesive (AD2746), basis polyurethane | 3 g/m² |
| PE peel foil, polyethylene | 40.0 μm |
| Aluminium type acc to AA 8021 (B) | AlFe 1.5 |

Coating formulation water-based and solvent-free O.B.A.-free (optical bleeching agent)

No recycled materials

Reference is again made to FIG. 1. As shown in FIG. 1, the container part 3 may further comprise one or more supporting elements 11 defining a set of support points or surfaces 12 distributed in a common horizontal plane below or in level with the outer surface of the bottom of the compartment 4. In the embodiment shown in FIG. 1, four such supporting elements 11 are present and the support points or surfaces 12 are distributed outside the bottom 9. By distributed outside the bottom 9 is meant that they are distributed away from the bottom and does not form part of the bottom. The container part 3 can preferably be made from one or more plastic(s), such as a thermoplastic plastic, preferably a thermoplastic polyester, for example selected from PBT (polybutylene terephthalate), PETG (polyethylene terephtalate glycol-modified) and PET (polyethylene terephthalate), preferably PET.

As shown in FIG. 1, the supporting elements 11 are downwardly protruding elements formed as indentations in the container part 3. The supporting elements 11 are produced in the same manner as the compartment 4 and preferably simultaneously with the compartment 4.

In the embodiment of FIG. 1, the support points or surfaces 12 are contained in a circumscribed rectangle of which the support points or a corner of each surface 12 defines the corners of the circumscribed reactangle and wherein geometrical centre of the circumscribed reactangle and the geometrical centre of the outer surface of the bottom of the compartment 4 coincide. This particular configuration of the compartment 4 and the supporting elements 11 has inter alia the advantage that the orientation of the container part 3 can be made easily, as the circumscribed rectangle has a longer and a short side. This can be utilised by shaping a depression in e.g. a conveyer to reflect the circumscribed rectangle whereby the container part 3 may only be received in a predefined orientation. Furthermore, as the supporting elements 11 are distributed outside the bottom 9, a container part 3 may be arranged on a surface without the risk of tilting.

Materials Used for the Container Part and Cover

Container part (3) is typically made from PET-GAG compliant with:

- Declaration of compliance for materials and articles intended to come into contact with food
    - 2002/72/EC and its supplements (COMMISSION DIRECTIVE 2002/72/EC of 6 Aug. 2002 relating to plastic materials and articles intended to come into contact with foodstuffs)—(now: 10/2011/EC)
    - 1935/2004/EC (REGULATION (EC) No 1935/2004 OF THE EUROPEAN PARLIAMENT AND OF THE COUNCIL of 27 Oct. 2004 on materials and articles intended to come into contact with food)
- 94/62/EC and its supplements (European Parliament and Council Directive 94/62/EC of 20 Dec. 1994 on packaging and packaging waste)
- conformity to CFR 21, part 170-199
- compliant to USP<661>'Physicochemical Test'
- DMF No 3764
- free of phthalates
- compliance with ISO 11607-1:2009 (Packaging for terminally sterilized medical devices. Requirements for materials, sterile barrier systems and packaging systems)
- ISO 9001 certified
- BrC:IoP certified Cover 7 is typically made from Tyvek® made by DuPont™ and complies with the following:

- 94/62/EC and its supplements
- Declaration of compliance for materials and articles intended to come into contact with food
    - 2002/72/EC and its supplements
    - 1935/2004/EC
    - 2023/2006/EC (COMMISSION REGULATION (EC) No 2023/2006 of 22 Dec. 2006 on good manufacturing practice for materials and articles intended to come into contact with food)
- free of phthalates
- DMF No 1893
- conformity to CFR 21, part 176.170(c)
- compliance with ISO 11607-1:2009
- ISO 13485:2003 certified Bag or Pouch Containing a Coiled Coated Carrier Further disclosed herein is a bag or pouch comprising or consisting of one or more waterproof material(s), the bag or pouch containing a coiled coated carrier. In particular, further disclosed herein is a bag or pouch comprising or consisting of one or more waterproof materials(s), said bag containing a coiled collagen carrier which comprises a collagen layer and a coating layer on top of the collagen layer, said coating layer comprising thrombin and fibrinogen, wherein said coiled collagen carrier has the shape of an elongated element with a number of windings of the collagen carrier about the longitudinal axis of the elongated element and at least one outer winding(s) of the carrier being orientated so that the coating layer constitutes the outer surface of each of said outer winding(s), wherein said coiled collagen carrier is form-stable and defines a collagen carrier in a coiled configuration where said outer winding(s) proceed along a spiral in a cross section of the collagen carrier.

The bag or pouch is preferably sterile. In one embodiment of the present invention, the collagen is pre-packed in the bag or pouch prior to application.

The bag or pouch may be sealed (for example, heat-sealed) on all sides and thus fully watertight or alternatively the bag or pouch may be open at one or more end(s) or side(s) to enable easy removal of the coiled collagen carrier. The bag or pouch can alternatively be opened by cutting or may be easy-to-open by pulling on a flap or by pulling on e.g. a peel-off flap or strip.

By a "waterproof" material is herein meant any material which is relatively unaffected by water or resists the ingress of water or moisture under normal temperature and pressure. Such a waterproof material can be used to reduce or prevent a coiled/rolled collagen carrier of the present invention from contacting blood or other liquids during preparation for surgery and/or during the surgery itself.

Examples of waterproof materials suitable for use in the present invention are one or more plastics (such as e.g. pvc and/or an x-ray detectable plastic, polyurethane, or nylon coated with Polyurethane) and/or flexible foils, such as aluminum foil. Surgical grade plastics are one preferred group of suitable waterproof material, such as e.g. surgical grade polyvinyl chloride (pvc), polyethylene terphthalate, polyurethane and also surgical grade silicone rubber materials. The material should preferably be flexible to allow easy manipulation in the form of a bag or pouch. A transparent waterproof material may be used in some instances, such as a transparent surgical grade plastic, like transparent pvc. It is preferred that the bag or pouch is sterile Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A packaging containing a form-stable coiled hemostatic collagen carrier, said form-stable coiled hemostatic collagen carrier comprising
    a collagen sponge;
    and a coating layer on a top surface of the collagen sponge and comprising thrombin and fibrinogen; and having the shape of an elongated element with a number of windings of the collagen carrier about the longitudinal axis of the elongated element with at least one outer winding,
    wherein the at least one outer winding is orientated so that the coating layer constitutes the outer surface of each outer winding, the packaging comprising
    a container part having a compartment in which at least a part of the coiled hemostatic collagen carrier is contained, the compartment having an opening with a rim, provided in an upper surface of the container part, and at least one cavity situated at the rim of the opening, wherein said cavity opens into the compartment and into the upper surface.

2. A packaging according to claim 1, wherein the opening is generally rectangular shaped having two longer sides and two shorter sides, wherein a length of the longer sides and a length of the shorter sides of the opening are larger than a length and a diameter, respectively, of the coiled hemostatic collagen carrier.

3. A packaging according to claim 2, wherein a cavity is situated at one of the shorter sides of the opening.

4. A packaging according to claim 2, wherein a cavity is situated at one of the longer sides of the opening.

5. A packaging according to claim 2, wherein the cavity comprises a wall section extending from a position at the upper surface outside the rim of the opening and towards the bottom of the compartment, wherein the wall section of the cavity extends sloped or curved.

6. A packaging according to claim 1, wherein the packaging comprises a cover covering the opening of the packaging.

7. A packaging according to claim 6, wherein the cover is attached to the container part and the attachment being configured for manual removal of the cover.

8. A packaging according to claim 6, wherein the cover is attached by a heat welding or a gluing to the upper surface of the container part.

9. A packaging according to claim 6, wherein the cover is attached to the container part along an outer rim of the container part encircling the opening and the cavity.

10. A packaging according to claim 6, wherein the cover has a pull-tab not being attached to the container part.

11. A packaging according to claim 6, wherein the cover is at least one of gas and liquid permeable.

12. A packaging according to claim 11, wherein the cover is made from a medical grade high density polyethylene sealing cover foil.

13. A packaging according to claim 1, wherein the container part is sheet-shaped, wherein the compartment and the cavity is formed as indentations in the sheet.

14. A packaging according to claim 1, wherein the container part is made from plastic.

15. A packaging according to claim 1, wherein the container part is thermoformed.

16. A packaging according to claim 1, wherein the upper surface of the container part is horizontal, and the compartment is cuboid shaped and comprises a horizontal bottom, two side walls and an end wall, having intersections between the horizontal bottom, the two side walls and the end wall.

17. A packaging according to claim 16, wherein the intersections of the bottom with the side walls and the end wall respectively are rounded.

18. A packaging according to claim 16, wherein the cavity extends from the upper surface of the container part and towards the horizontal bottom of the compartment.

19. A packaging according to claim 6, wherein the packaging further comprises a second container inside which the container part with coiled hemostatic collagen carrier and the cover is arranged, wherein the second container is made from a fluid tight material and is fluid-tight when closed.

20. A packaging according to claim 19, wherein the packaging further comprises a desiccant arranged inside the second container and outside the container part with coiled hemostatic collagen carrier and the cover.

21. A packaging according to claim 19, wherein the second container is in the form of a pouch inside which the container part with coiled hemostatic collagen carrier and the cover and a desiccant are arranged, the pouch being tear-openable or pull-openable.

22. A packaging according to claim 20, wherein the second container is in the form of a pouch inside which the container part with coiled hemostatic collagen carrier and the cover and the desiccant are arranged, the pouch being tear-openable or pull-openable.

23. A packaging according to claim 19, wherein the second container is made from a foil comprising or consisting of aluminum.

24. A packaging according to claim 1, wherein the container part further comprises one or more supporting elements defining a set of support points or surfaces distributed in a common horizontal plane below or at the level of the outer surface of the bottom of the compartment, the support points or surfaces being distributed outside the bottom.

25. A packaging according to claim 24, wherein the supporting elements are downwardly protruding elements formed as indentations in the container part.

26. A packaging according to claim 24, wherein the support points or surfaces are contained in a circumscribed rectangle of which the support points or a corner of each surface defines the corners of the circumscribed rectangle and wherein geometrical center of the circumscribed rectangle and the geometrical center of the outer surface of the bottom of the compartment coincide.

27. A packaging according to claim 22, wherein the container part further comprises one or more supporting elements defining a set of support points or surfaces distributed in a common horizontal plane below or at the level as the outer surface of the bottom of the compartment, the support points or surfaces being distributed outside the bottom, wherein the supporting elements are downwardly protruding elements formed as indentations in the container part, and the support points or surfaces are contained in a circumscribed rectangle of which the support points or a corner of each surface defines the corners of the circumscribed rectangle and wherein geometrical center of the circumscribed rectangle and the geometrical center of the outer surface of the bottom of the compartment coincide.

* * * * *